US006624302B2

United States Patent
Chu et al.

(10) Patent No.: US 6,624,302 B2
(45) Date of Patent: Sep. 23, 2003

(54) POLYKETIDE DERIVATIVES

(75) Inventors: Daniel Chu, Santa Clara, CA (US);
Maria Fardis, San Carlos, CA (US);
Chaitan Khosla, Palo Alto, CA (US);
Christopher Reeves, Orinda, CA (US);
Daniel Santi, San Francisco, CA (US);
Andreas Schirmer, Hayward, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 10/331,047

(22) Filed: Dec. 27, 2002

(65) Prior Publication Data
US 2003/0144315 A1 Jul. 31, 2003

Related U.S. Application Data

(63) Continuation of application No. 10/122,016, filed on Apr. 12, 2002, now abandoned, which is a continuation of application No. 09/853,306, filed on May 10, 2001, which is a continuation-in-part of application No. 09/410,551, filed on Oct. 1, 1999, now Pat. No. 6,503,737.
(60) Provisional application No. 60/252,968, filed on Nov. 22, 2000, provisional application No. 60/218,176, filed on Jul. 14, 2000, and provisional application No. 60/204,828, filed on May 17, 2000.

(51) Int. Cl.[7] ..................... C07D 498/16; C07D 498/18
(52) U.S. Cl. ..................................................... 540/456
(58) Field of Search ........................................ 540/456

(56) References Cited

U.S. PATENT DOCUMENTS

| | | | |
|---|---|---|---|
| 4,874,748 A | 10/1989 | Katz et al. | 514/29 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,189,042 A | 2/1993 | Goulet et al. | 514/291 |
| 5,672,491 A | 9/1997 | Khosla et al. | 435/148 |
| 5,712,146 A | 1/1998 | Khosla et al. | 435/252.35 |
| 5,824,513 A | 10/1998 | Katz et al. | 435/76 |
| 5,830,750 A | 11/1998 | Khosla et al. | 435/252.35 |
| 5,843,718 A | 12/1998 | Khosla et al. | 435/69.1 |
| 5,962,290 A | 10/1999 | Khosla et al. | 435/183 |
| 5,968,921 A | 10/1999 | Gold | 514/183 |
| 6,022,731 A | 2/2000 | Khosla et al. | 435/252.35 |
| 6,077,696 A | 6/2000 | Khosla et al. | 435/135 |
| 6,150,513 A | 11/2000 | Wu | 536/23.2 |
| 6,210,974 B1 | 4/2001 | Gold | 436/501 |

FOREIGN PATENT DOCUMENTS

| | | |
|---|---|---|
| EP | 0323042 A | 7/1989 |
| EP | 0356399 A | 2/1990 |
| EP | 0463690 A | 1/1992 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |
| WO | WO 00/20601 | 4/2000 |

OTHER PUBLICATIONS

Caffrey et al., 1992, *FEBS Letters 304*: 205.
Chen T.S. et al. (1992), "Microbial Transformation of Immunosupressive Compounds. II. Specific desmethylation of 13–methoxy group of FK 506 and FR 9500520 by Actinomycete sp. ATCC 53828," *J Antibiot* 45(4):577–580.
Dumont F.J. et al. (1992). "The Immunosupressive and Toxic Effects of FK–506 Are Mechanically Related: Pharmacology of a Novel Antagonist of FK–506 and Rapamycin," *J of Exp Medicine* 176(3):751–760.
Fu et al., 1994, *Biochemistry 33*: 9321–9326.
Gold et al., (1995) Journal of Neuroscience 15:7509–7516.
Gold et al., (1990) J. Pharm. Exp. Ther. 289(3):1202–1210.
Harrison's Principles of Internal Medicine, 14th Edition, 1998, McGraw Hill, Chapters 14,20,21,64–67.
Iwasaki et al., (1993) Drug Metabolism and Disposition 21:971–977.
Iwasaki et al., (1995) Drug Metabolism and Disposition 23:28–34.
Kawai et al., (1993) FEBS Letters 316(2):107–113.
Khosla C. (1997). "Harnessing the Biosynthetic Potential of Modular Polyketide Synthases," *Chemical Reviews* 97(7):2577–2590.
Lyons et al., (1994) Proc. Natl. Acad. Sci. USA 91:3191–3195.

(List continued on next page.)

*Primary Examiner*—Bruck Kifle
(74) *Attorney, Agent, or Firm*—Carolyn A. Favorito; Kate H. Murashige; Daniel P. Lentini

(57) ABSTRACT

The present invention relates to novel polyketides, host cells that produce the novel compounds, and methods fort their use. The compounds of the present invention are cyclic polyketides (also referred to as a "macrolides" or "macrolactones") that include

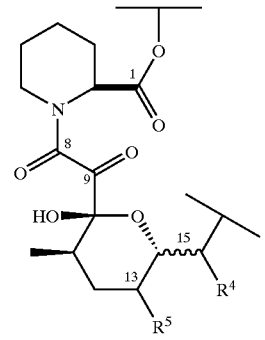

as part of their structure and bind to a FK binding protein wherein $R^4$ and $R^5$ are each selected from the group consisting of hydrogen, methyl, ethyl, and methoxy, provided that at least one of $R^4$ and $R^5$ is hydrogen, methyl, or ethyl. As will be explained in greater detail below, the compounds of the present invention have properties such as favorable P450 enzyme activity profiles that are desirable for use of these compounds as drugs.

12 Claims, 1 Drawing Sheet

OTHER PUBLICATIONS

McDaniel et al., 1993, *Science* 262: 1546–1550.
Motamedi et al., (1996) J. Bacteriol. 178:5243–5248.
Motamedi et al., (1997) Eur. J. Biochem. 244:78–80.
Motamedi and Shafiee, (1998) Eur. J. Biochem. 256:528.
Reynolds K.A. et al. (1997). "Rapamycin, FK 506, and Ascomycin–related Compounds," *Drugs Pharm Sci* 82:497–520.
Rohr, 1995, *Angew. Chem. Int. Ed. Engl.* 34(8): 881–888.
Shafiee A. et al. (1993). "Enzymatic synthesis and Immunosupressive Activity of Novel Desmethylated Immunomycins (Ascomycins)," *J Antibiot* 46(9):1397–1405.

Shiraga et al., (1994) Biochem. Pharmacol. 47:727–735.

Stassi D.L. et al. (1998). "Ethyl–substituted Erythromycin Derivatives Produced by Directed Metabolic Engineering," *Proc Natl Acad Sci USA* 95 (13):7305–7309.

Steiner et al., (1997) Proc. Natl. Acad. Sci. USA 94:2019–2024.

Vincent et al., (1992) Arch. Biochem. Biophys. 294:454–460.

Wu et al., (2000) Gene 251:81–90.

POLYKETIDE DERIVATIVES

CROSS REFERENCE TO RELATED APPLICATIONS

This application is a continuation of U.S. utility patent application Ser. No. 10/122,016, filed Apr. 12, 2003 now abandoned, which is a continuation of U.S. utility patent application Serial No.09/853,306, filed May 10, 2001, which is a continuation-in-part of U.S. utility patent application Ser. No. 09/410,551, filed Oct. 1, 1999 by inventors Christopher Reeves, Daniel Chu, Chaitan Khosla, Daniel Santi, and Kai Wu entitled POLYKETIDE SYNTHASE ENZYMES AND RECOMBINANT DNA CONSTRUCTS THEREFOR, now U.S. Pat. No. 6,503,737, and to U.S. provisional applications (i) Ser. No. 60/252,968 filed Nov. 22, 2000 by inventors Daniel Chu, Chaitan Khosla, Daniel Santi and Maria Fardis entitled NOVEL POLYKETIDE DERIVATIVES (ii) Ser. No. 60/218,176 filed Jul. 14, 2000 by inventors Daniel Chu, Chaitan Khosla, Daniel Santi, and Maria Fardis entitled METABOLICALLY STABLE DERIVATIVES OF FK-506 AND FK-520 and (iii) Ser. No. 60/204,828 filed May 17, 2000 by inventors Daniel Chu, Christopher Reeves, Chaitan Khosla, Daniel Santi and Maria Fardis entitled NOVEL POLYKETIDE DERIVATIVES, all of which are incorporated herein by reference in their entireties.

GOVERNMENT SUPPORT

This invention was made in whole or in part with government support from National Institute of Allergy and Infectious Diseases under SBIR Grant No. 1R43 AI46206-01-A1. Accordingly, the government may have certain rights in the invention.

BACKGROUND

Polyketides are a diverse class of compounds that are the source of many biologically active molecules such as tetracycline, erythromycin, epothilone, narbomycin, picromycin, rapamycin, spinocyn, and tylosin. Other important examples include naturally occurring immunosuppressants FK-506 (also known as tacrolimus) and FK-520 (also known as ascomycin).

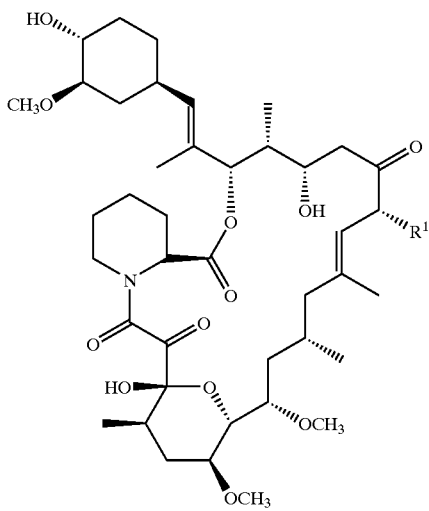

Differing by a single substituent ($R^1$) at C-21, FK-506 has an allyl group whereas FK-520 has an ethyl group at this position. Of the two, FK-506 has been particularly well studied and is used currently as an immunosuppressive drug.

FK-506 and FK-520 exert their biologic effects through the initial formation of an intermediate complex with proteins known as FKBPs (FK-506 binding proteins) such as FKBP-12 and FKBP-52. These proteins are a class of cytosolic proteins that form complexes with molecules such as FK-506, FK-520, and rapamycin that in turn serve as ligands for other cellular targets involved in signal transduction. Binding of FK-506, FK-520, and rapamycin to FKBP occurs through the structurally similar segments of the polyketide molecules, known as the "FKBP-binding domain" (as generally but not precisely indicated by the stippled regions in the structures below).

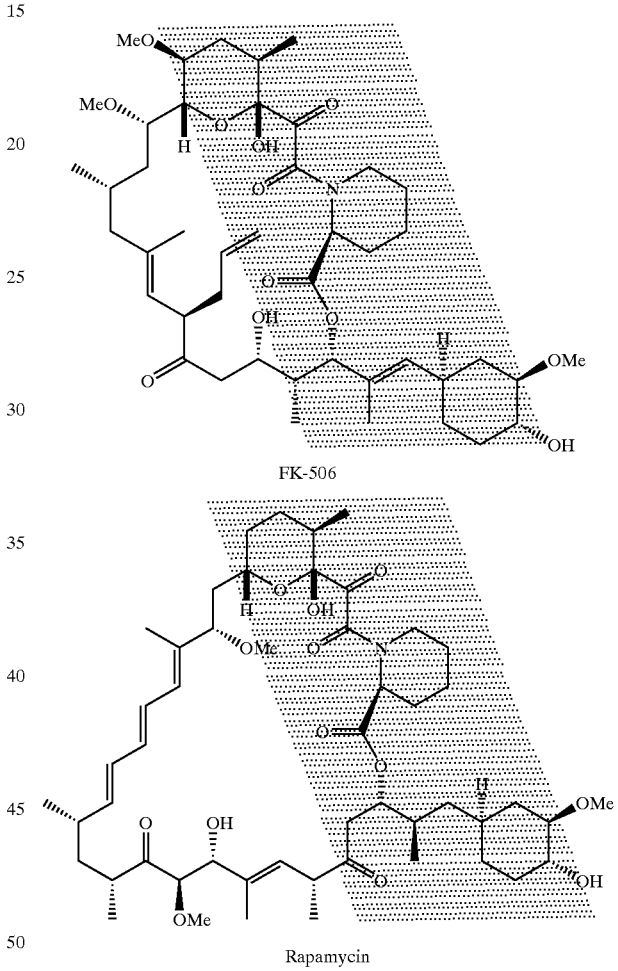

The FK-506-FKBP complex then binds calcineurin, while the rapamycin-FKBP) complex binds to a protein known as RAFT-1. Binding of the FKBP-polyketide complex to these second proteins occurs through the dissimilar regions of the drugs known as the "effector" domains.

The three component FKBP-polyketide-effector complex is required for signal transduction and subsequent immunosuppressive activity of FK-506, FK-520, and rapamycin. Modifications in the effector domains of FK-506, FK-520, and rapamycin that destroy binding to the effector proteins (calcineurin or RAFT) but leave FKBP binding unaffected lead to loss of immunosuppressive activity. Further, such analogs antagonize the immunosuppressive effects of the parent polyketides, because they compete for FKBP. Such non-immunosuppressive analogs also show reduced toxicity (see Dumont et al., 1992, *Journal of Experimental Medicine* 176, 751–760), indicating that much of the toxicity of these drugs is through a mechanism not mediated by FKBP binding.

In addition to immunosuppressive activity, FK-520, FK-506, and rapamycin have neurotrophic activity. In the central nervous system and in peripheral nerves, the corresponding target proteins are referred to as neuroproteins. The neuro-FKBP is markedly enriched in the central nervous system and in peripheral nerves. Molecules that bind to the neuro-FKBP, such as FK-506 and FK-520, have the remarkable effect of stimulating nerve growth. In vitro, they act as neurotrophins. More particularly, they promote neurite outgrowth in NGF-treated PC12 cells and in sensory neuronal cultures, and they promote regrowth of damaged facial and sciatic nerves, and repair lesioned serotonin and dopamine neurons in the brain in intact animals. See Gold et al., June 1999, *J. Pharm. Exp. Ther.* 289(3): 1202–1210; Lyons et al., 1994, *Proc. National Academy of Science* 91: 3191–3195; Gold et al., 1995, *Journal of Neuroscience* 15: 7509–7516; Steiner et al., 1997, *Proc. National Academy of Science* 94: 2019–2024; and U.S. Pat. Nos. 5,968,921 and 6,210,974. Further, the restored central and peripheral neurons appear to be functional.

Compared to protein neurotrophic molecules (e.g., BNDF, NGF, etc.), the small-molecule neurotrophins such as FK-506, FK-520, and rapamycin have different, and often advantageous properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neurconal processes and seem to affect damaged nerves specifically. Neuro-FKBP ligands have therapeutic utility in a variety of disorders involving nerve degeneration (e.g. multiple sclerosis, Parkinson's disease, Alzheimer's disease, stroke, traumatic spinal cord and brain injury, peripheral neuropathies).

The metabolism and pharmacokinetics of FK-506 have been extensively studied, and FK-520 is believed to be similar in these respects. Absorption of FK-506 is rapid, variable, and incomplete from the gastrointestinal tract (Harrison's Principles of Internal Medicine, 14th edition, 1998, McGraw Hill, 14, 20, 21, 64–67). The mean bioavailability of the oral dosage form is 27% (range 5 to 65%). The volume of distribution (VolD) based on plasma is 5 to 65 L per kg of body weight (L/kg), and is much higher than the VolD based on whole blood concentrations, the difference reflecting the binding of FK-506 to red blood cells. Whole blood concentrations may be 12 to 67 times the plasma concentrations. Protein binding is high (75 to 99%), primarily to albumin and alpha1-acid glycoprotein. The half-life for distribution is 0.9 hour; elimination is biphasic and variable: terminal-11.3 hours (range, 3.5 to 40.5 hours). The time to peak concentration is 0.5 to 4 hours after oral administration.

FK-506 is metabolized primarily by cytochrome P450 3A enzymes in the liver and small intestine. The drug is extensively metabolized with less than 1% excreted unchanged in urine. Because hepatic-dysfunction decreases clearance of FK-506, doses have to be reduced substantially in primary graft non-function, especially in children. In addition, the bioactivity of FK-506 is affected by drugs that modulate the activity of P450 3A enzymes. Drugs that induce the cytochrome P450 3A enzymes reduce FK-506 levels, while drugs that inhibit these P450s increase FK-506 levels. For example, FK-506 bioavailability doubles with co-administration of ketoconazole, a drug that inhibits P450 3A. See, Vincent et al., 1992, *Arch. Biochem. Biophys.* 294: 454–460; Iwasaki et al., 1993, *Drug Metabolism & Disposition* 21:971–977; Shiraga et al., 1994, *Biochem. Pharmacol.* 47: 727–735; and Iwasaki et al., 1995, *Drug Metabolism & Disposition* 23: 28–34.

FIG. 1 shows the eight isolated metabolic products formed from incubation of FK-506 with liver microscomes. As can be seen, four metabolites of FK-506 involve demethylation of the methoxy groups on carbons 13, 15, and 31, and hydroxylation of carbon 12. The 13-demethylated (hydroxy) compounds undergo cyclizations of the 13-hydroxy at carbon 10 to give M-I, M-VI and M-VII, and the 12-hydroxy metabolite at carbon 10 to give M-I. Another four metabolites formed by oxidation of the four metabolites mentioned above were isolated by liver microsomes from dexamethasone treated rats. Three of these are metabolites doubly demethylated at the methoxy groups on carbons 15 and 31 (M-V), 13 and 31 (M-VI), and 13 and 15 (M-VII). The fourth, M-VIII, was the metabolite produced after demethylation of the carbon 31-methoxy group, followed by formation of a fused ring system by further oxidation. Among the eight metabolites, M-II has immunosuppressive activity comparable to that of FK-506, whereas the other metabolites exhibit weak or negligible activities. Importantly, the major metabolite of human, dog, and rat liver microsomes (representing approximately about 90% of the metabolic products after a 10 minute incubation) is the 13-demethylated and cyclized FK-506 (M-I).

A disadvantage of using FK-506 and FK-520 as drugs is dosing unpredictability. Due to the significant variability in metabolism among patients, an appropriate dosing regimen is difficult to ascertain for an individual patient. Another disadvantage of FK-506 and FK-520 is their dual pharmacological effects as immunosuppressants and as neurotrophic agents. In general, compounds having a single specificity are desired. For example, a FK-506 like compound having only neurotrophic activity without immunosuppressive activity or vice versa may be used to treat the intended symptom without the side effects of the other bioactivity.

As a result, derivatives that improve upon the properties of FK-506 and FK-520 are needed and desired. However, because FK-506 and FK-520 are complex structures that are generally not amenable to either de novo chemical synthesis or facile derivation, this need remains unfulfilled.

SUMMARY

The present invention relates to novel polyketides, host cells that produce the novel compounds, and methods fort their use. The compounds of the present invention are cyclic polyketides (also referred to as a "macrolides" or "macrolactones") that include

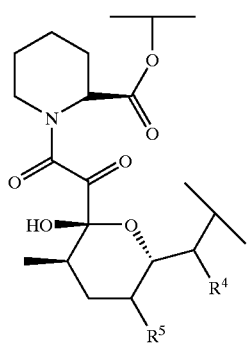

as part of their structure and bind to a FK binding protein wherein $R^4$ and $R^5$ are each selected from the group consisting of hydrogen, methyl, ethyl, and methoxy, provided that at least one of $R^4$ and $R^5$ is hydrogen, methyl, or ethyl. As will be explained in greater detail below, the compounds of the present invention have properties such as favorable P450 enzyme activity profiles that are desirable for use of these compounds as drugs.

DETAILED DESCRIPTION OF THE PREFERRED EMBODIMENTS

Figure 1:
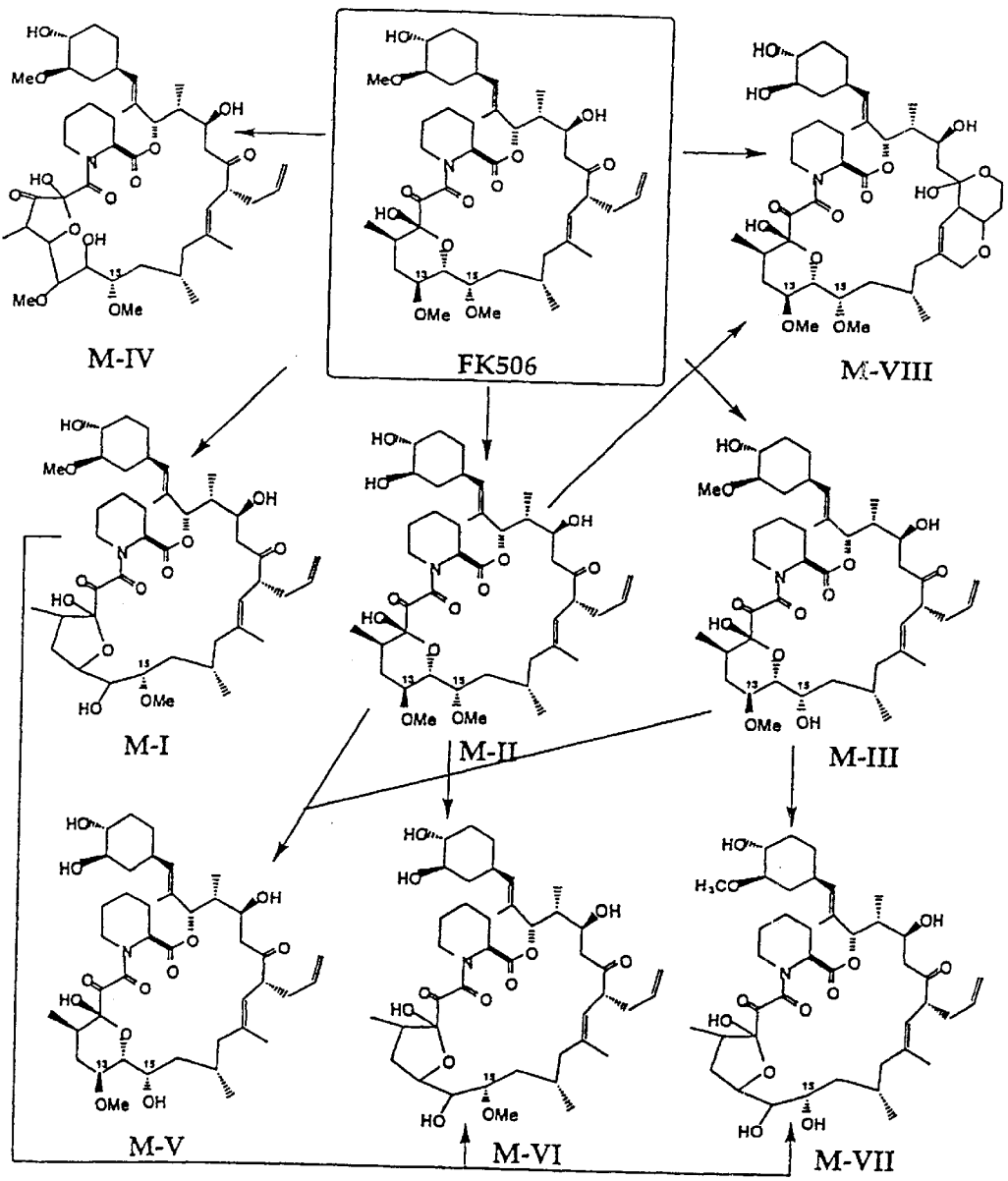
FIG. 1 shows the proposed degradative pathway for FK-506 metabolism.

The present invention relates to novel polyketides structurally related to FK-506 and FK-520 and to methods for making and using the same.

Definitions

The following general statements and terms are used to describe, the compounds of the present invention.

All stereoisomers of the inventive compounds are included within the scope of the invention, as pure compounds as well as mixtures thereof. Individual enantiomers, diastereomers, geometric isomers, and combinations and mixtures thereof are all encompassed by the present invention. Furthermore, some of the crystalline forms for the compounds may exist as polymorphs and as such are included in the present invention. In addition, some of the compounds may form solvates with water (i.e., hydrates) or common organic solvents, and such solvates are also encompassed within the scope of this invention.

Protected forms of the inventive compounds are included within the scope of the present invention. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form of the inventive compounds are those where at least one of the hydroxyl groups is protected by a hydroxy protecting group. Illustrative hydroxyl protecting groups include but not limited to tetrahydropyranyl; benzyl; methylthiomethyl; ethylthiomethyl; pivaloyl; phenylsulfonyl; triphenylmethyl; trisubstituted silyl such as trimethyl silyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl and the like; acyl and aroyl such as acetyl, pivaloylbenzoyl, 4-methoxybenzoyl, 4-nitrobenzoyl and aliphatic acylaryl and the like. Keto groups in the inventive compounds may similarly be protected.

The present invention includes within its scope prodrugs of the compounds of this invention. In general, such prodrugs are functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in "Design of Prodrugs", H. Bundgaard ed., Elsevier, 1985.

As used herein, the term "aliphatic" refers to saturated and unsaturated straight chained, branched chain, cyclic, or polycyclic hydrocarbons that may be optionally substituted at one or more positions. Illustrative examples of aliphatic groups include alkyl, alkenyl, alkynyl, cycloalkyl, cycloalkenyl, and cycloalkynyl moieties. The term "alkyl" refers to straight or branched chain saturated hydrocarbon substituent. "Alkenyl" refers to a straight or branched chain hydrocarbon substituent with at least one carbon-carbon double bond. "Alkynyl" refers to a straight or branched chain hydrocarbon substituent with at least one carbon-carbon triple bound.

The term "aryl" refers to monocyclic or polycyclic groups having at least one aromatic ring structure that optionally include one ore more heteroatoms and preferably include three to fourteen carbon atoms. Aryl substituents may optionally be substituted at one or more positions. Illustrative examples of aryl groups include but are not limited to: furanyl, imidazolyl, indanyl, indenyl, indolyl, isooxazolyl, isoquinolinyl, naphthyl, oxazolyl, oxadiazolyl, phenyl, pyrazinyl, pyridyl, pyrimidinyl, pyrrolyl, pyrazolyl, quinolyl, quinoxalyl, tetrahydronaphththyl, tetrazolyl, thiazolyl, thienyl, and the like.

The term "heteroaryl" is an aryl that includes one or more hetero atoms such as O, N, and S.

The aliphatic (i.e., alkyl, alkenyl, etc.) and aryl moieties may be optionally substituted with one or more substituents, preferably from one to five substituents, more preferably from one to three substituents, and most preferably from one to two substituents. The definition of any substituent or variable at a particular location in a molecule is independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include but are not limited to: alkyl, alkenyl, alkynyl, aryl, halo; trifluoromethyl; trifluoromethoxy; hydroxy; alkoxy; cycloalkoxy; heterocyclooxy; oxo; alkanoyl (—C(=O)-alkyl which is also referred to as "acyl")); aryloxy; alkanoyloxy; amino; alkylamino; arylamino; aralkylamino; cycloalkylamino; heterocycloamino; disubstituted amines in which the two amino substituents are selected from alkyl, aryl, or aralkyl; alkanoylamino; aroylamino; aralkanoylamino; substituted alkanoylamino; substituted arylamino; substituted aralkanoylamino; thiol; alkylthio; arylthio; aralkylthio; cycloalkylthio; heterocyclothio; alkylthiono; arylthiono; aralkylthiono; alkylsulfonyl; arylsulfonyl; aralkylsulfonyl; sulfonamido (e.g., $SO_2NH_2$); substituted sulfonamido; nitro; cyano; carboxy; carbamyl (e.g., CONH$_2$); substituted carbamyl (e.g., —C(═O)NRR' where R and R' are each independently hydrogen, alkyl, aryl, aralkyl and the like); alkoxycarbonyl, aryl, substituted aryl, guanidino, and heterocyclo such as indoyl, imidazolyl, furyl, thienyl, thiazolyl, pyrrolidyl, pyridyl, pyrimidyl and the like. Where applicable, the substituent may be further substituted such as with, alkyl, alkoxy, aryl, aralkyl, halogen, hydroxy and the like.

The terms "alkylaryl" or "arylalkyl" refer to an aryl group with an aliphatic substituent that is bonded to the compound through the aliphatic group. An illustrative example of an alkylaryl or arylalkyl group is benzyl, a phenyl with a methyl group that is bonded to the compound through the methyl group (—CH$_2$Ph where Ph is phenyl).

The term "alkoxy" refers to —OR wherein O is oxygen and R is an aliphatic group.

The term "hydroxyalkyl" refers to —ROH where R is an aliphatic moiety.

In addition to the explicit substitutions at the above-described groups, the inventive compounds may include other substitutions where applicable. For example, the lactone backbone or backbone substituents may be additionally substituted (e.g., by replacing one of the hydrogens or by derivatizing a non-hydrogen group) with one or more substituents such as C$_1$–C$_5$ aliphatic, C$_1$–C$_5$ alkoxy, aryl, or a functional group. Illustrative examples of suitable functional groups include but are not limited to: acetal, alcohol, aldehyde, amide, amine, boronate, carbamate, carboalkoxy, carbonate, carbodiimide, carboxylic acid, cyanohydrin, disulfide, enamine, ester, ether, halogen, hydrazide, hydrazone, imide, imido, imine, isocyanate, ketal, ketone, nitro, oxime, phosphine, phosphonate, phosphonic acid, quaternary ammonium, sulfenyl, sulfide, sulfone, sulfonic acid, thiol, and the like.

The term "FKBP" refers to a protein (of greater than 90% purity) that binds FK-506 with a K$_d$ (equilibrium binding constant) that is approximately equal to or less than about 1 µM in an in vitro assay. Illustrative examples of FKBPs include but are not limited to FKBP-12, (U.S. Pat. No. 5,109,112), FKBP-12.6 (U.S. Pat. No. 5,457,182), FKBP-13 (U.S. Pat. No. 5,498,597), FKBP-14.6 (U.S. Pat. No. 5,354,845), FKBP-52 (U.S. Pat. No. 5,763,590), FKBP-56 and FKBP-80, the patents which are incorporated herein by reference.

The term "isolated" as used herein to refer to a compound of the present invention, means altered "by human intervention from its natural state. For example, if the compound occurs in nature, it has been changed or removed from its original environment, or both. In other words, a compound naturally present in a living organism is not "isolated," but the same compound separated from the coexisting materials of its natural state is "isolated". However, with respect to compounds found in nature, the compound is isolated if that compound is substantially free of the materials with which that compound is associated in its natural state.

The term "purified" as it refers to a compound means that the compound is in a preparation that is substantially free of contaminating or undesired materials. The term purified can also mean that the compound forms a major component of the preparation, such as constituting about 50%, about 60%, about 70%, about 80%, about 90%, about 95% or more by weight of the components in the preparation.

The term "subject" as used herein, refers to an animal, preferably a mammal, who has been the object of treatment, observation or experiment and most preferably a human who has been the object of treatment and/or observation.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of one or more of the inventive compounds. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where tile compounds of the invention carry an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxyethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethioidide, undecanoate, valerate, and the like.

The term "pharmaceutically acceptable carrier" is a medium that is used to prepare a desired dosage form of the inventive compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe, ed. (Amer. Pharmaceutical Assoc. 2000), both of which are incorporated herein by reference in their entireties, disclose various carriers used in formulating pharmaceutical compositions and known techniques for the preparation thereof.

The term "pharmaceutically acceptable ester" is an ester that hydrolzyes in vivo into a compound of the present invention or a salt thereof. Illustrative examples of suitable ester groups include, for example, those derived from pharmaceutically acceptable aliphatic carboxylic acids such as formates, acetates, propionates, butyrates, acrylates, and ethylsuccinates.

Compounds of the Present Invention

In general, the compounds of the present invention are cyclic polyketides (also referred to as a "macrolides" or "macrolactones") that include

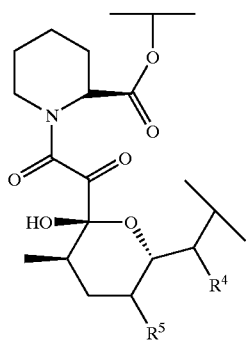

I as part of their structure and bind to a FKBP wherein $R^4$ and $R^5$ are each selected from the group consisting of hydrogen, methyl, ethyl, and methoxy, provided that at least one of $R^4$ and $R^5$ is hydrogen, methyl, or ethyl. In preferred embodiments, the FKBP is FKBP-12 or FKBP-52. In more preferred embodiments, the FKBP is FKBP-12 and the compound binds to FKBP-12 with a $K_d$ that is approximately equal to or less than about 100 nM. Compounds of the present invention that bind to FKBP-12 with a $K_d$ in the low nanomolar range (e.g., 50 nM, 25 nM, 10 nM, 5 nM, 1 nM, and 0.1 nM) are even more preferred.

In one aspect of the present invention, compounds are of the formula

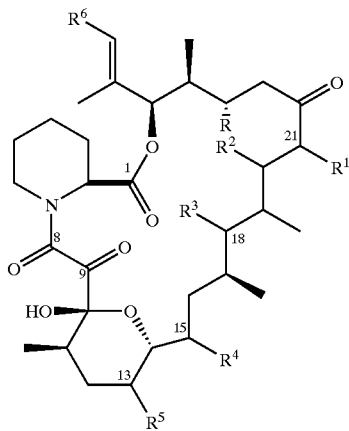

II are provided wherein:
R is hydroxyl;
$R^1$ is selected from the group consisting of hydrogen, methyl, propyl, ethyl and allyl;
$R^2$ and $R^3$ are each independently hydrogen or hydroxyl;
$R^4$ and $R^5$ are each independently selected from the group consisting of hydrogen, hydroxyl, methyl, ethyl, and methoxy, provided that at least one of $R^4$ and $R^5$ is hydrogen, methyl, or ethyl;

$R^6$ is selected from a group consisting

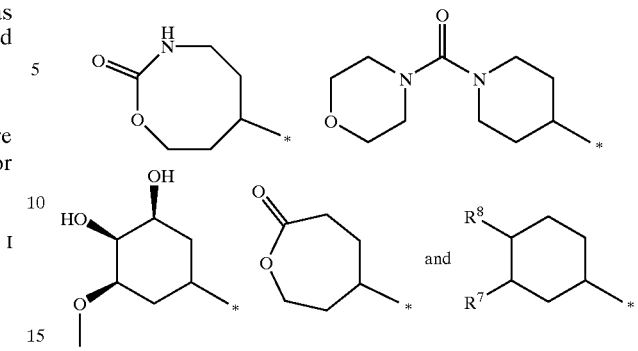

and wherein $R^7$ is selected from the group consisting of hydrogen, hydroxyl, methyl, ethyl, and methoxy and $R^8$ is selected from a group consisting of hydrogen, hydroxyl, $C_1$–$C_{10}$ alkyl, $C_1$–$C_{10}$ alkoxy, aryl, aryloxy, arylalkyl, and arylalkoxy; and,
a double bond exists between carbon-19 and carbon-20, or
a double bond exists between carbon-18 and carbon-19 and R and $R^2$ together are oxygen forming a lactone ring.

In one embodiment, the compounds are of formula I or II where $R^1$, $R^2$, $R^3$, $R^4$, $R^5$, $R^6$, $R^7$, and $R^8$ are as previously defined provided that FK-506, FK-520, 13-desmethoxy-FK-520, and 13-desmethoxy-13-methyl-FK520, 18-hydroxy-FK-520, and 18-hydroxy-FK-506 are excluded.

In another aspect of the invention, compounds of the formula:

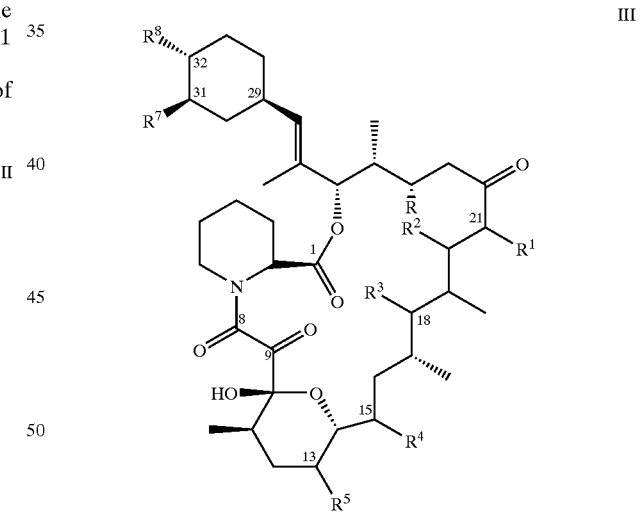

III are provided wherein:
R is hydroxyl;
$R^1$ is selected from the group consisting of hydrogen, methyl, ethyl, and allyl;
$R^2$ and $R^3$ are each independently hydrogen or hydroxyl;
$R^4$ and $R^5$ are each independently selected from the group consisting of hydrogen, hydroxyl, methyl, ethyl, and methoxy, provided that at least one of $R^4$ and $R^5$ is hydrogen, methyl, or ethyl;
$R^7$ and $R^8$ are each independently selected from a group consisting of hydrogen, hydroxyl, $C_1$–$C_{10}$ alkyl, $C_1$–$C_{10}$ alkoxy, aryl, aryloxy, arylalkyl, and arylalkoxy; and, a double bond exists between carbon-19 and carbon-20, or a double bond exists.between carbon-18 and carbon-19 and R and R2 together are oxygen forming a lactone ring.

In one embodiment, the compounds are of formula III wherein

R is hydroxyl;

$R^1$ is selected from the group consisting of hydrogen, methyl, ethyl, and allyl;

$R^2$ and $R^3$ are each independently hydrogen or hydroxyl;

$R^4$ and $R^5$ are each independently selected from the group consisting of hydrogen, hydroxyl, methyl, ethyl, and methoxy, provided that at least one of $R^4$ and $R^5$ is hydrogen, methyl, or ethyl;

$R^7$ is selected from the group consisting of hydrogen, hydroxyl, methyl, ethyl, $C_1$–$C_5$ alkoxy and aryloxy;

$R^8$ is selected from a group consisting of hydrogen, hydroxyl, wherein $R^9$ is selected from the group consisting of hydrogen, hydroxyl, halide, $C_1$–$C_5$ alkyl, $C_1$–$C_5$ hydroxyalkyl, and $C_1$–$C_5$ alkoxy; and, a double bond exists between carbon-19 and carbon-20, or a double bond exists between carbon-18 and carbon-19 and R and $R^2$ together are oxygen forming a lactone ring.

In another aspect of the present invention, the compounds of the formula

IV are provided wherein $R^1$ is ethyl or allyl;

$R^3$ is hydrogen or hydroxyl;

$R^4$, $R^5$ and $R^7$ are each independently selected from the group consisting of hydrogen, hydroxyl, methyl, ethyl, and methoxy; and $R^8$ is selected from a group consisting of hydrogen, hydroxyl, $C_1$–$C_5$ alkoxy, and heteroaryloxy, provided that at least one of $R^4$ and $R^5$ is hydrogen, methyl or ethyl.

In one embodiment, the compounds are of formula IV wherein $R^1$ is ethyl;

$R^3$ is hydrogen or hydroxyl;

$R^4$ and $R^5$ are each independently selected from the group consisting of hydrogen, hydroxyl, methyl, ethyl, and methoxy;

$R^7$ is methoxy; and, $R^8$ is hydroxyl.

In another embodiment, the compounds are of formula IV wherein $R^1$ is ethyl;

$R^3$ is hydrogen or hydroxyl;

$R^4$ is selected from the group consisting of hydrogen, hydroxyl, methyl, and ethyl;

$R^5$ is methoxy;

$R^7$ is methoxy; and, $R^8$ is hydroxyl.

In another embodiment, the compounds are of formula IV wherein

R$^1$ is ethyl;

R$^3$ is hydrogen or hydroxyl;

R$^4$ is selected from the group consisting of hydrogen, hydroxyl, methyl, and ethyl;

R$^5$ is ethyl;

R$^7$ is methoxy; and,

R$^8$ is hydroxyl.

In another aspect of the present invention, compounds of the formula

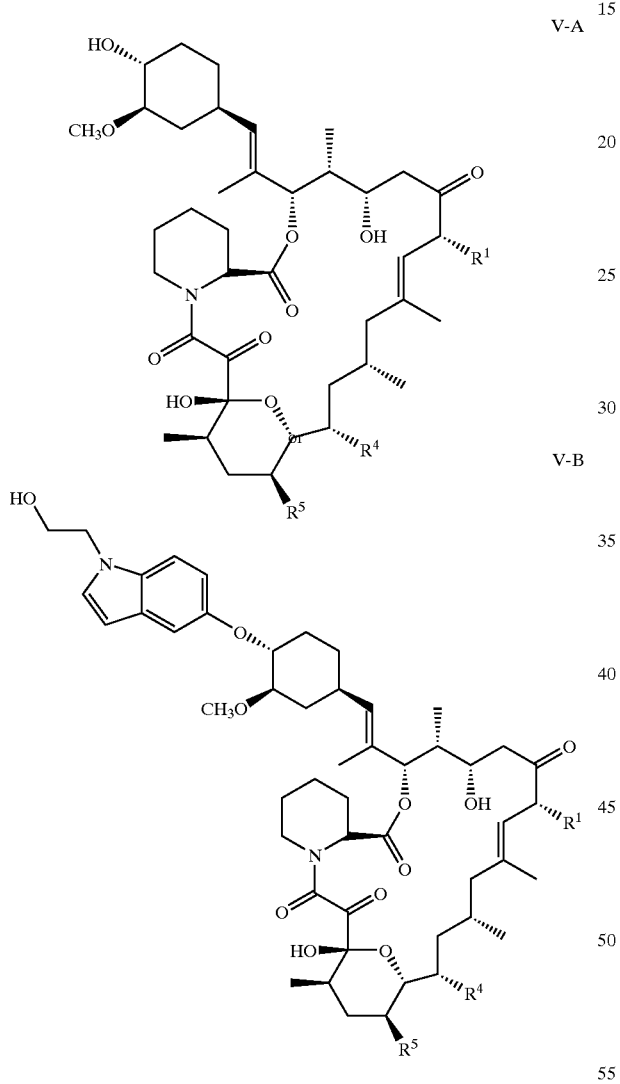

are provided wherein

R$^1$ is ethyl or allyl; and

R$^4$ and R$^5$ are each independently selected from the group consisting of hydrogen, hydroxyl, methyl, ethyl, and methoxy; provided that at least one of R$^4$ and R$^5$ is hydrogen, methyl or ethyl. These compounds are particularly preferred for use as immunosuppressants. Examples of compounds of formulas V-A and V-B include but are not limited to those listed in Table 1.

TABLE 1

| Formula | R$^1$ | R$^4$ | R$^5$ |
|---|---|---|---|
| V-A or V-B | allyl | methoxy | hydrogen |
| V-A or V-B | allyl | methoxy | methyl |
| V-A or V-B | allyl | methoxy | ethyl |
| V-A or V-B | allyl | hydrogen | hydrogen |
| V-A or V-B | allyl | hydrogen | methyl |
| V-A or V-B | allyl | hydrogen | ethyl |
| V-A or V-B | allyl | hydrogen | methoxy |
| V-A or V-B | allyl | methyl | hydrogen |
| V-A or V-B | allyl | methyl | methyl |
| V-A or V-B | allyl | methyl | ethyl |
| V-A or V-B | allyl | methyl | methoxy |
| V-A or V-B | ethyl | methoxy | hydrogen |
| V-A or V-B | ethyl | methoxy | methyl |
| V-A or V-B | ethyl | methoxy | ethyl |
| V-A or V-B | ethyl | hydrogen | hydrogen |
| V-A or V-B | ethyl | hydrogen | methyl |
| V-A or V-B | ethyl | hydrogen | ethyl |
| V-A or V-B | ethyl | hydrogen | methoxy |
| V-A or V-B | ethyl | methyl | hydrogen |
| V-A or V-B | ethyl | methyl | methyl |
| V-A or V-B | ethyl | methyl | ethyl |
| V-A or V-B | ethyl | methyl | methoxy |

In another aspect of the present invention, compounds having targeted specificity are provided. In one embodiment, compounds of the formula

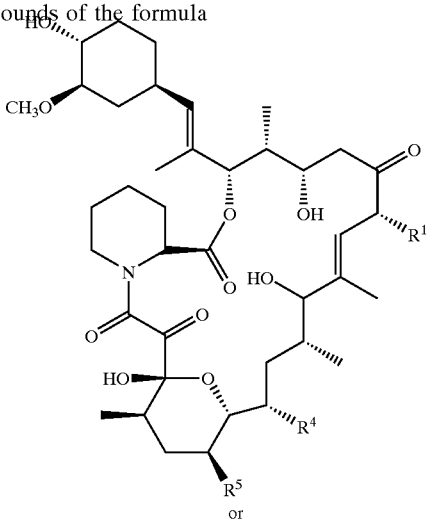

or

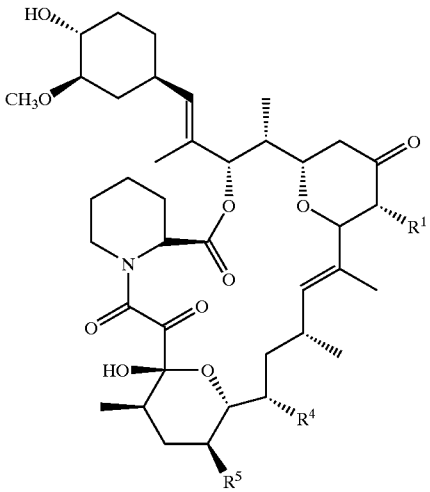

are provided wherein $R^1$ is ethyl or allyl;

$R^4$ and $R^5$ are each independently selected from the group consisting of hydrogen, hydroxyl, methyl, ethyl, and methoxy; provided that at least one of $R^4$ and $R^5$ is hydrogen, methyl or ethyl. These compounds possess neurotrophic activity without also possessing immunosuppressive activity so are particularly preferred for use as neurotrophic agents. Examples of compounds of formulas VI-A and VI-B include but are not limited to those listed in Table 2.

TABLE 2

| Formula | $R^1$ | $R^4$ | $R^5$ |
| --- | --- | --- | --- |
| VI-A or VI-B | allyl | methoxy | hydrogen |
| VI-A or VI-B | allyl | methoxy | methyl |
| VI-A or VI-B | allyl | methoxy | ethyl |
| VI-A or VI-B | allyl | hydrogen | hydrogen |
| VI-A or VI-B | allyl | hydrogen | methyl |
| VI-A or VI-B | allyl | hydrogen | ethyl |
| VI-A or VI-B | allyl | hydrogen | methoxy |
| VI-A or VI-B | allyl | methyl | hydrogen |
| VI-A or VI-B | allyl | methyl | methyl |
| VI-A or VI-B | allyl | methyl | ethyl |
| VI-A or VI-B | allyl | methyl | methoxy |
| VI-A or VI-B | ethyl | methoxy | hydrogen |
| VI-A or VI-B | ethyl | methoxy | methyl |
| VI-A or VI-B | ethyl | methoxy | ethyl |
| VI-A or VI-B | ethyl | hydrogen | hydrogen |
| VI-A or VI-B | ethyl | hydrogen | methyl |
| VI-A or VI-B | ethyl | hydrogen | ethyl |
| VI-A or VI-B | ethyl | hydrogen | methoxy |
| VI-A or VI-B | ethyl | methyl | hydrogen |
| VI-A or VI-B | ethyl | methyl | methyl |
| VI-A or VI-B | ethyl | methyl | ethyl |
| VI-A or VI-B | ethyl | methyl | methoxy |

In another aspect of the present invention, compounds of the formula VI-A are provided wherein $R^1$ is ethyl;

$R^4$ is methoxy; and, $R^5$ is selected from the group consisting of hydrogen, hydroxyl, methyl, and ethyl.

In another aspect of the present invention, compounds of the formula VI-A are provided wherein $R^1$ is ethyl;

$R^4$ is ethyl; and, $R^5$ is selected from the group consisting of hydrogen, hydroxyl, methyl, and ethyl.

Because all of the above described FK-like compounds lack a methoxy group at carbon 13 and/or carbon 15 and/or carbon 31 (which are referred to as C-13 desmethoxy, C-15 desmethoxy, and C-31 desmethoxy respectively), the initial demethylation reactions to which FK-506/FK-520 are subjected by one or more P450 enzymes do not occur, thus modulating the normal FK-506/FK-520 metabolism.

Methods for Making the Inventive Compounds

The compounds of the present invention can be made, for example, by the genetic manipulation of the FK-520 or FK-506 polyketide synthase ("PKS") gene in a FK-520 or a FK-506 producing host cell alone or in combination with subsequent chemical modification of the compounds.

The nucleotide sequence of the FK-520 PKS gene from *Streptomyces hygroscopicus* var. *ascomycetiucus* (ATCC 14891) has been deposited in GenBank and assigned Accession No. AF235504. Cosmids, pKOS034–124 (ATCC PTA-729), pKOS034-120 (ATCC PTA-728), pKOS065-M27 (ATCC PTA-726), and pKCOS065-M21 (ATCC PTA-727) containing overlapping fragments of the FK-520 PKS gene have been deposited with the American Type Culture Collection, 10801 University Blvd., Manassas Va., 20110-2209 USA ("ATCC") on Sep. 20, 1999.

FK-520 derivatives are generally made by the expression of these and modified constructs in suitable host cells such as those that normally produce FK-520. FK-506 derivatives may be made analogously. Alternatively, the recombinant PKS constructs can be expressed in a heterologous host cell as described in U.S. Pat. Nos. 5,672,491 and 6,033,883 and PCT publication No. WO 99/02699, each of which is incorporated herein by reference.

For the purposes of illustration, an abbreviated description is provided for making novel recombinant PKS constructs using the FK-520 PKS gene. The FK-520 PKS enzyme is composed of the fkbA, fkbB, fkbC, and fkbP gene products and synthesizes the core structure of the FK-520 molecule. The fkbB open reading frame encodes the loading module and the first four extender modules of the PKS. The fkbC open reading frame encodes extender modules five and six of the PKS. The fkbA open reading frame encodes extender modules seven, eight, nine, and ten of the PKS. The fkbP open reading frame encodes the non-ribosomal peptide synthetase of th PKS that attaches the pipecolic acid moiety and cyclizes the resulting polyketide.

The polyketide product of the PK-520. PKS is subjected to several post-synthetic modifications to form FK-520. The keto group at C-9 is formed from a hydroxylation reaction mediated by the fkbD gene product, a P450 hydroxylase, followed by an oxidation reaction mediated by the fkbO gene product. The C-31 methoxy group is formed from a methylation reaction that is mediated by the fkbM gene product, an O-methyltransferase. The C-13 and C-15 methoxy groups are believed to be formed by methylation reactions by a methyltransferase that is believed to be encoded by the fkbG gene. This methyltransferase is believed to act on the hydroxymalonyl CoA substrates prior to binding of the substrate to the AT domains of the PKS during polyketide synthesis.

Any of fkbA, fkbB, fkbC, fkbP, fkbD, fkbG, fkbM and fkbO genes either individually or collectively may be modified in the practice of the present invention to make novel FK-derivatives. The modifications may be in the genes that encode the PKS or in the genes that encode one or more of the tailoring enzymes. An illustration of a modification in a tailoring enzyme is, for example, deletion of the methyltransferase activity encoded by the fkbM gene to yield a compound of the invention having a hydroxyl group at C-31.

Other modifications include alterations in the specificity and/or activity of one or more domains that comprise the PKS. In an illustrative embodiment, the AT domain of module 4 is replaced with a malonyl specific AT domain to provide a PKS that produces 21-desethyl-FK520, or is replaced with a methylmalonyl specific AT domain to provide a PKS that produces 21-desethyl-21-methyl-FK520.

In another illustrative embodiment, the KR and DH coding sequences of module 5 are replaced with those encoding only a KR domain from another PKS gene. The resulting PKS genes code for the expression of an FK-520 PKS that produces an FK-520 analog that lacks the C-19 to C-20 double bond of FK-520 and has a C-20 hydroxyl group. Alternatively, the DH domain of module 5 may be deleted or otherwise rendered inactive.

In another example, the coding sequences for extender module six is replaced with those for an extender module having a methylmalonyl specific AT and only a KR domain from a heterologous PKS gene, such as, for example, the coding sequences for extender module two encoded by the eryAI gene. The resulting PKS genes code for the expression of an FK-520 PKS that produces an FK-520 analog that has a C-18 hydroxyl group. Alternatively, the DH and ER domains of module 6 may be deleted or otherwise rendered inactive.

In another illustrative embodiment, the AT domain of module 7, which specifies a methoxymalonyl CoA and from which the C-15 methoxy group of FK-520 is derived is replaced by an AT domain that specifies a malonyl, methylmalonyl or ethylmalonyl CoA. Examples of such replacement AT domains include the AT domains from modules 2, 3, and 14 of the rapamycin PKS, modules 1 and 2 of the erythromycin (DEBS) PKS, and module 4 of the FK-520 PKS. Constructs where module 7 is replaced with an AT domain from extender module 2 or extender module 14 of the rapamycin PKS result in a PKS that produces 15-desmethoxy FK-520 (hydrogen at C-15). Constructs with Preferably, such hybrid PKS enzymes are produced in recombinant Streptomyces host cells that produce FK-520 but have been mutated to inactivate the gene whose function is to be replaced, for example by the rapamycin PKS gene to make the hybrid PKS. Particular examples include (i) replacement of the respective fkbC gene with the rapB gene; and (ii) replacement of the respective fkbA gene with the rapC gene. The latter hybrid PKS produces 13,15-didesmethoxy-FK-520.

A number of engineered strains of *Streptomyces Hygroscopicus* var. *ascomycetiucus* ATCC 14891 that produce novel compounds of the present invention have been deposited with the ATCC or with the Agricultural Research Service Culture Collection, 1815 North University Street, Peoria, Ill. 61604 USA ("NRRL") as summarized in Table 3.

TABLE 3

| Strain[a] | Deposit Site | Compound Produced |
|---|---|---|
| KOS45-170 (PTA-1811) | ATCC on 05/03/00 | 13-desmethoxy-FK-520 |
| KOS60-135 (PTA-1810) | ATCC on 05/03/00 | 13-desmethoxy-13-methyl-FK-520 |
| KOS132-188 | NRRL on 04/17/01 | 13,15-bisdesmethoxy-FK-520 |
| KOS132-191 | NRRL on 04/17/01 | 13,15-bisdesmethoxy-15-methyl-FK-520 |
| KOS156-25 | NRRL on 04/17/01 | 13,15-bisdesmethoxy-15-ethyl-FK-520 |
| KOS156-9A | NRRL on 04/17/01 | 15-desmethoxy-FK-520 |
| KOS156-9B | NRRL on 04/17/01 | 15-desmethoxy-15-methyl-FK-520 |
| KOS156-26 | NRRL on 04/17/01 | 15-desmethoxy-15-ethyl-FK-5201 |
| KOS156-33A | NRRL on 04/17/01 | 13,15-bismethoxy-13-methyl-FK-520 |
| KOS156-33B | NRRL on 04/17/01 | 13,15-bismethoxy-13-methyl-15-methyl-FK-520 |
| KOS156-33C | NRRL on 04/17/01 | 13,15-bismethoxy-13-methyl-15-methyl-FK-520 |

[a]An alternate strain name is where the "KOS" portion of the strain name is replaced with a "K". For example strain KOS132-188 may be referred to as K132-188.

an AT domain from extender module 3 from the rapamycin PKS or from extender modules 1 or 2 of the erythromycin (DEBS) PKS provide a PKS that produces 15-desmethoxy-15-methyl-FK520. Constructs with an AT domain from extender module 4 of the FK-520 PKS provide a PKS that produces 15-desmethoxy-15-ethyl FK-520.

In another example, the AT domain of module 8, which specifies a hydroxymalonyl CoA and from which the C-13 methoxy group of FK-520 is derived, is replaced by an AT domain that specifies a malonyl, methylmalonyl, or ethylmalonyl CoA. Examples of such replacement AT domains include the AT domains from modules 3, 12, and 13 of the rapamycin PKS and from modules 1 and 2 of the erythromycin PKS. For example, strain KOS60-135 is derived from *Streptomyces hygroscopicus* (ATCC 14891) and expresses a recombinant FK-520 PKS in which the AT domain of extender module 8 has been replaced by the AT domain of extender module 3 of the rapamycin PKS. KOS60-135 produces 13-desmethoxy-13-methyl-FK520. Similarly, strain KOS45–170 is derived from *Streptomyces hygroscopicus* (ATCC 14891) and expresses a recombinant FK-520 PKS in which the AT domain of extender module 8 has been replaced by the AT domain of extender module 12 of the rapamycin PKS. KOS45-170 produces 13-desmethoxy-FK-520.

In addition to the above, the desired stereochemistry of a particular two carbon unit may be achieved by replacing its module (or one or more domains of the module) with another module (or one or more domains of the module) having the desired stereochemistry.

Instead of modifying the individual modules of fkbA, fkbB, and fkbC, the entire gene may be replaced by another.

These strains and the compounds they produced are embodiments of the present invention.

Methods for making these and other host cells of the invention that produces bioengineered FK-520 derivatives and FK-506 derivatives are also described in U.S. Ser. No. 09/410,551 filed Oct. 1, 1999 by inventors Christopher Reeves, Daniel Chu, Chaitan Khosla, Daniel Santi, and Kai Wu entitled POLYKETIDE SYNTHASE ENZYMES AND RECOMBINANT DNA CONSTRUCTS THEREFOR which is incorporated herein by reference.

Host cells can be grown and fermented and the novel FK-derivatives they produce can be isolated and purified from the fermentation broth of these cells using standard procedures. Example 2 describes a fermentation method for growing host cells using trypic soy broth with reference to the fermentation of KOS45-170 (which produces 13-desmethoxy-FK-520). Example 3 describes an alternate fermentation method with reference to KOS60-135 (which produces 13-desmethoxy-13-methyl-FK-520). Other host cells of the invention may be grown using either method by substituting the desired host cell for KOS45-170 in Example 2 or for KOS60–130 in Example 3.

Examples 4and 5 describe the purification and characterization of 13-desmethoxy-FK-520 from the fermentation of KOS45-170. Examples 6 and 7 describe the purification of 13-desmethoxy-13-methyl-FK-520 from the fermentation of KOS60-135. See also, U.S. Pat. Nos. 5,194,378; 5,116,756; and 5,494,820, each of which is incorporated herein by reference. Example 8 describes a general purification protocol from fermentation and summarizes the $^{13}$C-NMR data for select compounds of the present invention.

Optional Chemical Derivation

Once the FK-derivatives of the present invention have been isolated, they may be further modified using synthetic methods. See e.g. Advanced Organic Chemistry 3rd Ed. by Jerry March (1985) which is incorporated herein by reference.

For example, although compounds having a hydroxyl at C-18 can be made genetically by altering module six or fkbC of the FK-520 or FK-506 PKS gene, they can also be made by subsequent chemical modification. A particularly effective selective hydroxylation can be achieved at C-18 by using a general selenium dioxide protocol described by Umbreit and Sharpless, 1977, JACS 99(16): 1526–28 that has been modified for use with FK-like compounds. The procedure generally involves an ene reaction with selenic acid followed by a [2,3] sigmatropic rearrangement. Briefly, about 1 equivalent of an inventive compound is reacted with about 1.5 equivalents of $SeO_2$ and about 7 equivalents of t-BuOOH, preferably in the presence of some water, to yield the corresponding 18-hydroxy-FK-derivative. Example 9 describes the direct hydroxylation method in greater detail with reference to the C-18 hydroxylation of 13-desmethoxy-13-methyl-FK-520. The 18-ene, 20 oxa derivatives are made by treating an optionally protected 18-hydroxy compound with acid. Example 10 describes this method in greater detail with reference the synthesis of 18-ene-20-oxa-13-desmethoxy-13-methyl-FK-520.

Chemical modifications can also be made at C-32. In one method, a metal halogen exchange reaction is used where a halogenated compound ("ZX" wherein X is a halogen) is reacted with for example, nBuli, to form the corresponding lithiated compound, ZLi. The lithiated halogen compound (ZLi) becomes ligands for bismuth upon reacting with $BiCl_3$ (yielding $BiZ_3$). The bismuthane resulting from reaction of $BiZ_3$ with benzoyl peroxide is reacted with a compound of interest to yield the corresponding FK-derivative with Z at the C-32 position. Scheme 1 is a schematic illustration of one embodiment of this method where tris[1-(2-t-butyldimethylsilyloxyethyl)indol-5-yl]bismuthane is used to make 32-[1-(2-hydroxyethyl)-indol-5-yl]-compounds.

SCHEME 1

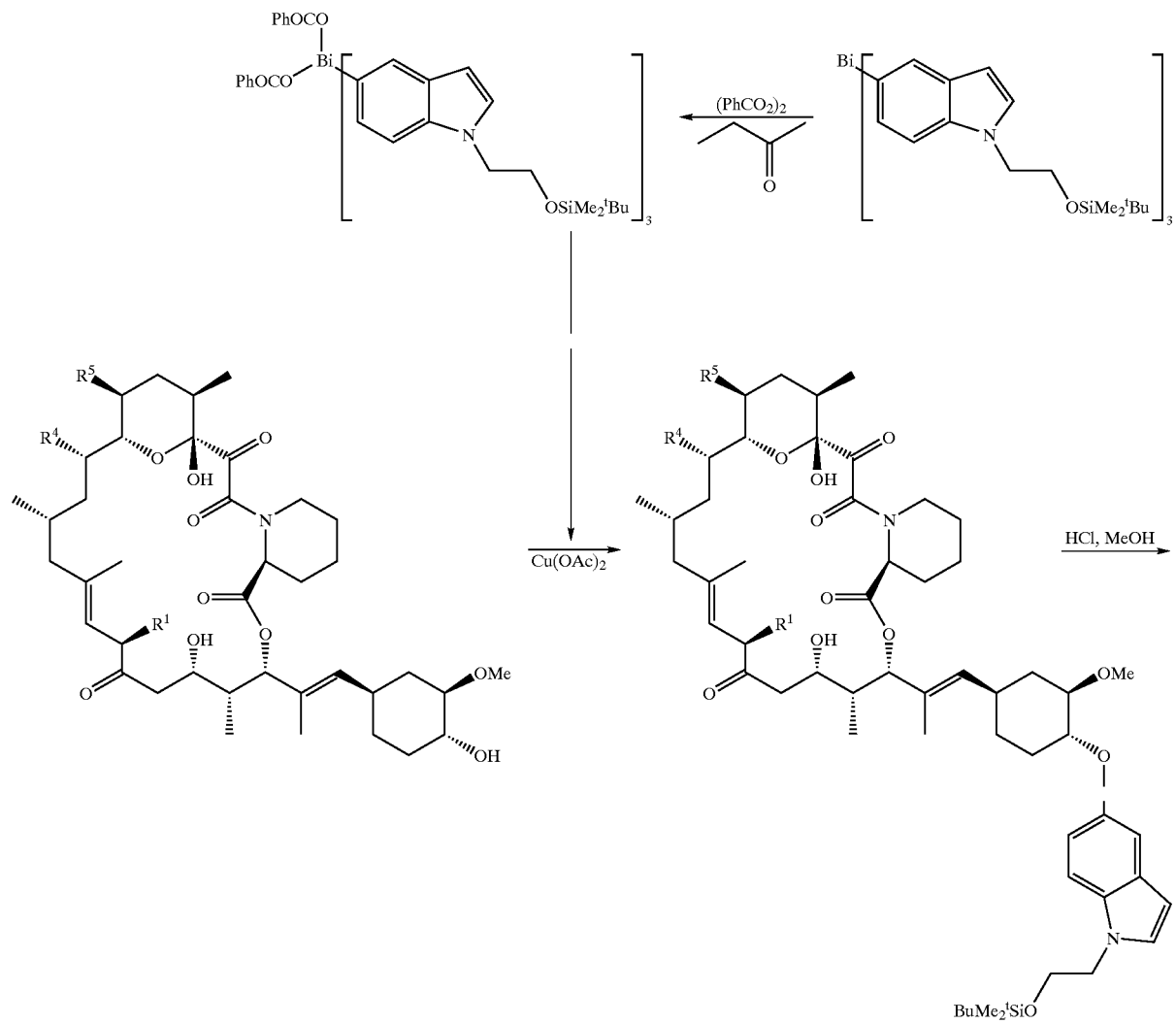

-continued

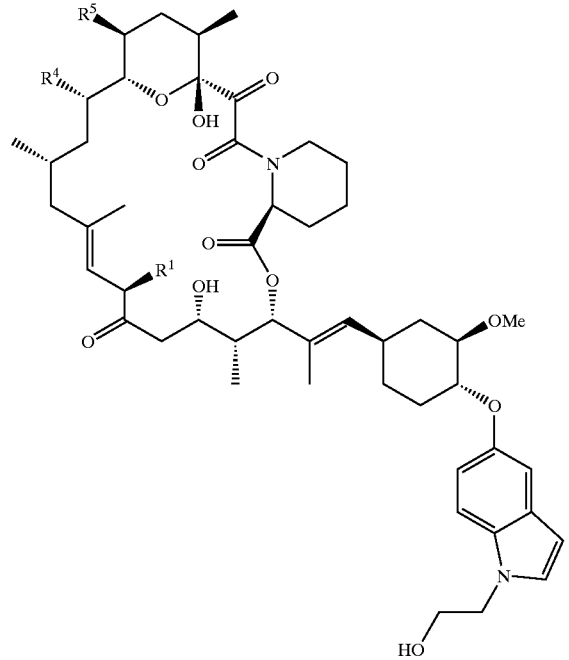

Detailed protocols are found in the Examples. Example 10 describes an illustrative protocol for making 1-(2-hydroxyethyl)-5-bromoindole from 5-bromoindole and for making the corresponding bismuthane. Examples 11 and 12 describe the use of tris[1-(2-t-butyldimethylsilyloxyethyl)indol-5-yl]bismuthane to make 32-[1-(2-Hydroxyethyl)-indol-5-yl]-13-desmethoxy-13-methyl-FK-520 and 32-[1-(2-Hydroxyethyl)-indol-5-yl]-13-desmethoxy-FK-520 respectively.

Another method for making C-32 derivatives involves converting the hydroxyl group at this position into a better leaving group and then subsequently displacing the group with a moiety of interest. Scheme 2 describes two illustrative protocols.

Scheme 2

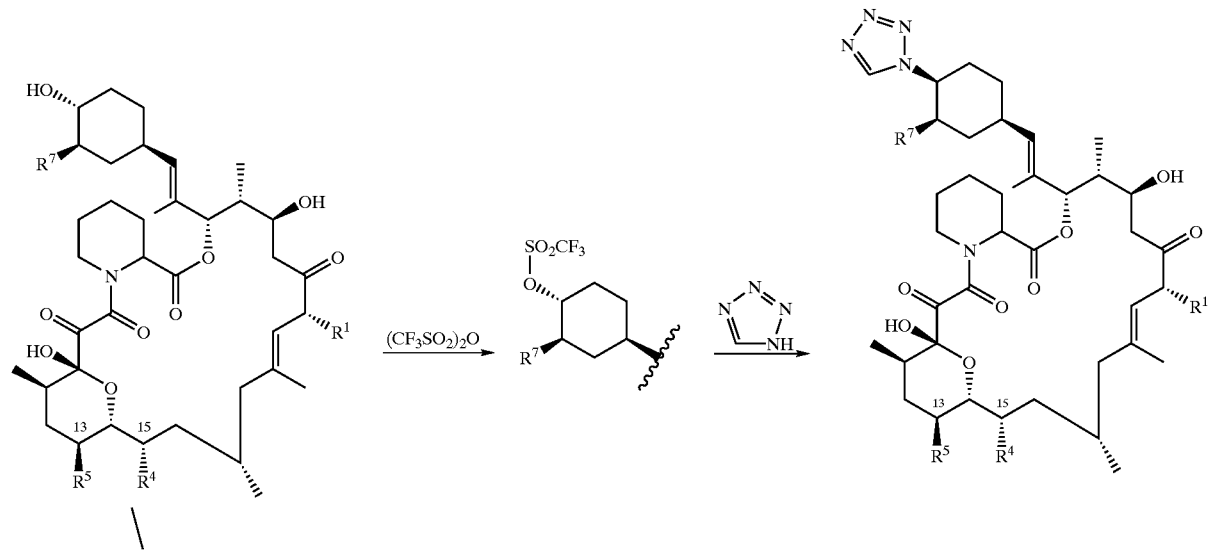

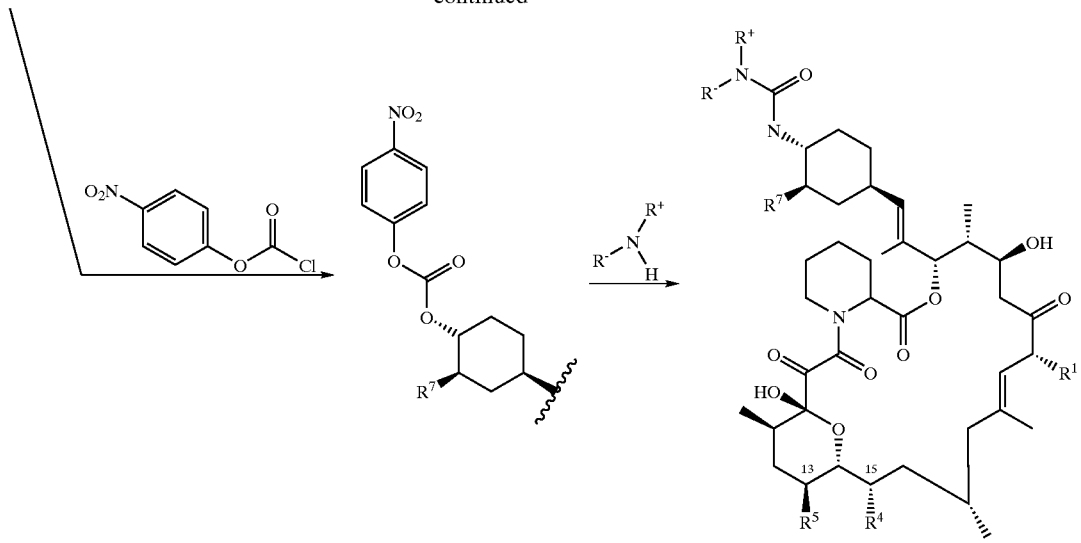

In the first reaction shown in Scheme 2, a compound of the present invention is selectively reacted with trifluoromethanesulfonlic an hydride in the presence of a base to yield the C-32 O-triflate derivative. SN2-displacement of the triflate with aryl compounds such as 1H-tetrazole provides the corresponding C-32 aryl derivative. This strategy is particularly effective when the moiety of interest is a poor nucleophile.

In the second reaction shown in Scheme 2, the hydroxyl at C-32 is displaced with a good nucleophile. Here, the inventive compound is reacted with p-nitrophenylchloroformate to yield the corresponding carbonate. The p-nitropilenol is subsequently displaced with an amino compound to provide the corresponding carbamate derivative.

Other chemical modifications include C-32-O-aralkyl ethers. These compounds can be made by following the procedure described by Goulet et al., 1998, Bioorg. Med. Chem. Lett. 8: 2253–2258, which is incorporated herein by reference. Derivatives with a=N—NH(C=O)NH$_2$ moiety at C-32 can be made using a protocol described by Example 19 of U.S. Pat. No. 5,604,294, which is incorporated herein by reference. U.S. Pat. Nos. 4,894,366; 5,247,076; 5,252,732; 5,349,061; 5,457,111; 5,877,184 and 6,504,294 describe making additional modifications at the cyclohexyl ring and are also incorporated herein by reference. Chemical modifications can also be made at the C-31 position in compounds possessing a C-31 hydroxyl that are similar to those described for the C-32 hydroxyl. Modifications where the cyclohexyl ring is replaced with other moieties are described by U.S. Pat. No. 5,612,350 which is also incorporated herein by reference.

Formulation

A composition of the present invention generally comprises one or more compound of the present invention and a pharmaceutically acceptable carrier. The inventive compound may be in free form or where appropriate as pharmaceutically acceptable derivatives such as prodrugs, and salts and esters of the inventive compound.

The one or more compounds of the present invention are included in the pharmaceutical composition in an amount sufficient to produce the desired effect upon the disease process or condition. In preferred embodiments, the amount of activie ingredient may range between about 0.01 mg to 50 mg and more preferably between about 0.1 mg to 10 mg. In even more preferred embodiments, the amount of active ingredients range from about 0.5 mg to about 5 mg. Convenient dosages amounts include 0.5 mg, 1 mg and 5 mg units.

The composition may be in any suitable form such as solid, semisolid, or liquid form (e.g., tablets, pellets, capsules, suppositories, solutions, emulsions, suspensions, etc.). See Pharmaceutical Dosage Forms and Drug Delivery Systems, 5$^{th}$ edition, Lippicott Williams & Wilkins (1991) which is incorporated herein by reference. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquefied form. In addition, auxiliary stabilizing, thickening, and coloring agents and perfumes may be used.

Where applicable, an inventive compound may be formulated as microcapsules and nanoparticles. General protocols are described for example, by Microcapsules and Nanoparticles in Medicine and Pharmacy by Max Donbrow ed., CRC Press (1992) and by U.S. Pat. Nos. 5,510,118; 5,534,270; and 5,662,883 which are all incorporated herein by reference. By increasing the ratio of surface area to volume, these formulations allow for the oral delivery of compounds that would not otherwise be amenable to oral delivery.

An inventive compound may also be formulated using other methods that have been previously used for low solubility drugs. For example, the compounds may form emulsions with vitamin E or a PEGylated derivative thereof as described by PCT Publications WO 98/30205 and WO 00/71163 which are incorporated herein by reference. Typically, the inventive compound is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another strategy involves encapsulating the inventive compounds in liposomes.

Yet another method involves formulating an inventive compound using polymers such as polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters polyamides polyorthoesters and some polyphosphazenes. Illustrative examples of naturally occurring polymers include proteins and polysaccharides such as collagen, hyaluronic acid, albumin, and gelatin.

Another method involves conjugating a compound of the present. invention to a polymer that enhances aqueous solubility. A particularly effective method involves conjugating polyethylene glycol or a poly-amino acid such as poly-glutamic acid or poly-aspartic acid via ester linkages to one or more hydroxyl groups (e.g. such as off carbons 10, 24 and where applicable, off carbon 18) of the compound. Illustrative examples of suitable polymers include polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyethylene glycol conjugated compounds can also be made as essentially described by U.S. Pat. No. 5,922,729 which is incorporated herein by reference. Poly-amino acid conjugated compounds, particularly poly-glutamic acid conjugated compounds may be prepared as described by U.S. Pat. No. 5,977,163 which is incorporated herein by reference.

In another method, an inventive compound is conjugated to a monoclonal antibody. This strategy allows the targeting of the inventive compound to specific targets. General protocols for the design and use of conjugated antibodies are described in Monoclonal Antibody-Based Therapy of Cancer by Michael L. Grossbard, ed. (1998), which is incorporated herein by reference.

In addition, specific formulations previously described for FK-506 can be adapted for use with the inventive compounds. For example, U.S. Pat. No. 5,955,469 and PCT Publication No. WO 99/49863, which are incorporated herein by reference, provide methods for making emulsions for all applications including oral and intravenous use. U.S. Pat. Nos. 5,939,427 and 5,385,907, and PCT Publication Nos. 96/13249, 99/24036, and 00/32234, which are also incorporated herein by reference, describe lotion and ointment formulations.

U.S. Pat. Nos. 5,338,684 and 5,260,301 describe solution formulations for intravenous use and for injections. Briefly, due to the relatively poor solubility of the inventive compounds in water, the compounds of the present invention are admixed with a castor-oil type surface active agent such as HCO (polyoxyethylated castor oil, most preferably HCO-60 (trademark, prepared by Nikko Chemicals Co.), and/or admixed with an organic solvent, most preferably ethanol. As a result, formulations may comprise a compound of the present invention and polyoxyethylated castor oil and/or ethanol. An illustrative example of such a formulation comprises 5 mg of anhydrous Compound, 200 mg of polyoxyl 60 hydrogenated castor oil (HCO-60) and dehydrated ethanol USP, 80% v/v. This formulation can be packaged in 1 mL single dose ampules and can optionally be diluted with 0.9% sodium chloride or 5% dextrose solution prior to intravenous use.

Methods of Treating Patients

The compounds of the present invention are useful in treating disease conditions as described for FK-506 (also known as tacrolimus) in U.S. Pat. Nos. 5,955,469; 5,542,436; 5,365,948; 5,348,966; and 5,196,437, incorporated herein by reference. In one embodiment, the inventive compounds and compositions are used as immunosuppressive agents. In another embodiment, the inventive compounds and compositions are used as neurotrophic agents. In yet another embodiment, the inventive compounds and composition are used as agents to treat anti-inflammatory disorders, particularly inflammatory skin diseases such as psoriasis and dermatitis. The method generally comprises administering a therapeutically effective amount of an inventive compound to a subject in need thereof.

The compounds of the present invention are administered on an as-need basis and may be given to patients continuously or an intermittent basis, such as hourly, semi-daily, daily, semi-weekly, weekly, semi-monthly, or monthly intervals. In general, the dosage is the minimum amount of compound that is needed to effectuate the desired effect.

When the Compound is taken internally, a useful marker of determining the appropriate dosage is the whole blood trough concentration which should generally range from 0.01 picomole of drug per 1 mL of whole blood (1 picomole/mL) to 50 picomole of drug per 1 ml of whole blood (0.01 picomole/mL). In preferred embodiments, the dosage is the amount required to maintain a whole blood trough concentration of between about 1 picomole/mL and about 30 picomole/mL, and more preferably, between about 10 picomole/mL and about 20 picomole/mL. Moles are used to express the amounts of compound since weight amounts are dependent on the molecular weight of a particular Compound.

When the compounds of the present invention are used as immunosuppressants, they may be used in a similar manner as FK-506. To that end, although many parameters are expected to be different due to the metabolic stability of the compounds of the present invention, the pharmacological values for FK-506 provide useful benchmarks for comparisons and may be found on the internet at the following URL: http://www.fujisawausa.com/medinfo/pi/pi_page_pg.htm which is incorporated herein in its entirety.

There are a number of advantages of using the compounds of the present invention over that of using FK-506. One benefit is that the inventive compounds are metabolized more slowly than FK-506 enabling lower dosages and/or fewer numbers of doses per unit time period. For example, if the inventive compound is being administered by continuous intravenous infusion, a lower dosage may be used instead of the amount equivalent (in moles) to 0.03–0.05 mg/kg/day that is recommended for FK-506. If the inventive compound is being administered orally, then lower dosages may also be used instead of the amount that is equivalent to between about 0.05 and 0.10 mg/kg every twelve hours. Alternatively, the same amount may be used but because the compounds of the present invention are metabolized more slowly, they may be administered less frequently. For example, the amount that is equivalent to an oral dose of between about 0.05 and 0.10 mg/kg of FK-506 may be administered daily instead of every twelve hours. Finally, a combination of lower dose and less frequent administration may be used.

Another benefit is fewer drug interactions since the Inventive compounds are not significantly affected by P450 activity. As a result, a larger arsenal of drugs available to treat complications that may occur. For example, a common side effect of taking FK-506 is hypertension. Because commonly used anti-hypertensive agents are calcium channel blockers that modulate P450 activity levels and thus blood level of FK-506, treating patients with both FK-506 and a calcium channel blocker may be problematic. In contrast, no such problems are anticipated with the compounds of the present invention. If a patient being treated with an Inventive compound described herein develops hypertension, then that patient may be treated using a method comprising administering a compound of the present invention to treat the underlying ailment and administering an anti-hypertensive agent. Because the compounds are more resistant to P450 mediated metabolism, calcium channel blocking agents such as diltiazem, nicardipine, nifedipine, and verapamil may be more readily used.

Other examples of drugs that elevate FK-506 levels but may be used more readily with compounds of the present invention include but are not limited to: antifungal agents (such as clotrimazole, fluconazole, itraconazole, and ketoconazole); macrolide antibiotics (such as clarithromycin, erythromycin, troleandomycin); gastrointestinal prokinetic agents (such as cisapride and metoclopramide); and miscellaneous drugs such as bromocriptine, cimetidine, cyclosporine, danazol, methylprednisolone, and protease inhibitors. Examples of drugs that decrease FK-506 levels that may now be used more readily with a compound of the present invention include anticonvulsants (such as carbamazepine, phenobarbital, phenytoin) and antibiotics (such as rifabutin, and rifampin).

Use of the compounds of the present invention as neurotrophic agents (including dosing protocols) are generally similar to those outlined above for use as immunosuppressants. The benefits of using compounds of the present invention that are more metabolically stable over compounds like FK-506 and FK-520 are identical to that described above.

For the reasons stated above, practice of the present invention results in potentially fewer side effects and toxicities from the generally lower drug concentrations. Additional benefits include convenience for both patient and health care provider. In particular, blood levels of the compounds described herein do not need to be monitored as carefully or as frequently since individual variations in P450 activity are less important in the metabolism rate of these compounds and fewer drug-drug interactions are expected. Consequently, a standardized dosing schedule may be developed that is more generally applicable.

A detailed description of the invention having been provided above, the following examples are given for the purpose of illustrating the present invention and shall not be construed as being a limitation on the scope of the invention or claims.

EXAMPLE 1

Recombinant PKS Genes for FK-506 and FK-520 Compounds Having Variations at C-13 and C-15 Positions This Example provides construction protocols for recombinant FK-520 (*Streptomyces hygroscopicus* (ATCC 14891)) and FK-506 (from *Streptomyces* sp. MA6858 (ATCC 55098)), described in U.S. Pat. No. 5,116,756, incorporated herein by reference) PKS genes in which the extender module 7 and/or extender module 8 AT coding sequences have been replaced with an AT domain from another PKS. The AT domains of extender module 7 and 8 of FK-520 and FK-506 are believed t o specify methoxymalonyl CoA from which the methoxy groups at both C-13 and C-15 are derived. Replacement of the AT domains of extender module 7 and/or 8 with an AT domain that specifies other CoA esters such as malonyl CoA, methylmalonyl CoA and ethylmalonyl CoA results in compounds having a hydrogen, methyl, or ethyl at the C-13 and C-15 positions. Table 4 summaries the AT domains, their CoA specificities and the resulting group at the C-13/C15 positions.

TABLE 4

| AT DOMAIN | AT DOMAIN ORIGIN | AT SPECIFICITY | RESULTING GROUP |
|---|---|---|---|
| rapAT2 | extender module 2 of rapamycin PKS | malonyl CoA | hydrogen |
| rapAT12 | extender module 12 of rapamycin PKS | malonyl CoA | hydrogen |
| rapAT14 | extender module 14 of rapamycin PKS | malonyl CoA | hydrogen |
| eryAT2 | extender module 2 of erythromycin (DEBS) PKS | methyl malonyl CoA | methyl |
| rapAT3 | extender module 3 of rapamycin PKS | methyl malonyl CoA | methyl |
| FK520AT4 | extender module 4 of FK-520 PKS | ethyl malonyl CoA | ethyl |

Phage vector KC515 (based on the broad host range phage ΦC31) is used to deliver a cassette containing the AT domain to be swapped. The cassette contains one of the above heterologous AT domain inserted between two ca. 1.5 kb fragments of DNA identical to the sequences flanking AT7 or AT8. The resulting recombinant phage is used to transform the FK-520 or FK-506 producer strains. The transformed strains are cultured to select and identify desired recombinants produced by double crossover homologous recombination to yield the desired recombinant cells. See also, Examples 1–5 of U.S. Ser. No. 09/410,551 filed Oct. 1, 1999 which is incorporated herein by reference.

Table 5 includes an illustrative list of recombinant cells that produces inventive compounds having hydrogen, methyl or ethyl at the C-13 and/or C15 positions.

TABLE 5

| TARGET AT DOMAIN(S) | REPLACEMENT AT DOMAIN(S) | COMPOUND PRODUCED IN FK520 PRODUCING HOST | COMPOUND PRODUCED IN FK-506 PRODUCING HOST |
|---|---|---|---|
| AT8 | rapAT12 | 13-desmethoxy-FK-520 (KOS45-170) | 13 desmethoxy-FK-506 |
| AT8 | rapAT3 | 13-desmethoxy-13-methyl-FK-520 (KOS60-135) | 13-desmethoxy-13-methyl-FK-506 |
| AT7 | rapAT2 | 15-desmethoxy-FK-520 (KOS156-9A) | 15-desmethoxy-FK-506 |
| AT7 | rapAT3 | 15-desmethoxy-15-methyl-FK-520 (KOS156-9B) | 15-desmethoxy-15-methyl-FK-506 |
| AT7 | FK520AT4 | 15-desmethoxy-15-ethyl-FK-520 (KOS156-26) | 15-desmethoxy-15-ethyl-FK-506 |
| AT8 AT7 | rapAT12 rapAT2 | 13,15-bisdesmethoxy-FK-520 (KOS132-188) | 13,15-bismethoxy-FK-506 |
| AT8 AT7 | rapAT12 rapAT3 | 13-desmethoxy-15-desmethoxy-15-methyl-FK-520 (KOS132-191) | 13-desmethoxy-15-desmethoxy-15-methyl-FK-520 |
| AT8 AT7 | rapAT12 FK520AT4 | 13-desmethoxy-15-desmethoxy-15-ethyl-FK-520 (KOS156-25) | 13-desmethoxy-15-desmethoxy-15-ethyl-FK-506 |
| AT8 AT7 | rapAT3 rapAT14 | 13-desmethoxy-13-methyl-15-desmethoxy-FK-520 (KOS156-33A) | 13-desmethoxy-13-methyl-15-desmethoxy-FK-506 |
| AT8 AT7 | rapAT3 eryAT2 | 13,15-bisdesmethoxy-13,15-bismethyl-FK-520 (KOS156-33B) | 13,15-bisdesmethoxy-13,15-bismethyl-FK-520 |
| AT8 AT7 | rapAT3 FK520AT4 | 13-desmethoxy-13-methyl-15-desme-thoxy-15-ethyl-FK520 (KOS156-33C) | 13-desmethoxy-13-methyl-15-desme-thoxy-15-ethyl-FK506 |

These strains and the compounds they produced are embodiments of the present invention.

EXAMPLE 2

Production of 13-Desmethoxy-FK-520

A 1 mL vial of KOS-45-170 working cell bank was thawed arid the contents of the vial were added to 50 mL trypic soy broth in a 250 mL baffled flask. Trypic soy broth was purchase from Difco and a solution made at a concentration of 30 g/L. Prior to sterilization, the pH was adjusted to 6.0 and this solution was used as Medium 1. For growth in flasks, Medium 1 was supplemented with Prior to sterilization, 21.32 g/L of MES buffer prior to sterilization. 20 mL/L of 500 g/L glucose (sterile filtered) was added post-sterilization. The flask was placed in an incubator/shaker maintained at 30±1° C. and 175±25 RPM for 48±10 hours. The 50 mL culture was then added to a 2.8 L baffled flask containing 500 mL of medium. This flask was incubated in an incubator/shaker at 30±1° C. and 175±25 RPM for 48±10 hours.

A 10 L fermenter was prepared by sterilizing 10 L of Medium 1 at 121° C. for 60 minutes. 0.2 L of sterile filtered 500 g/L glucose was added to the 10 L fermenter. After incubation, the 500 ml culture was transferred to a sterile inoculation bottle and aseptically added to the 10 L fermenter. The fermenter was controlled at 30° C., pH 6.0 by addition of 2.5 N $H_2SO_4$ and 2.5 N NaOH, dissolved oxygen ≧50% air saturation by agitation rate (600–900 RPM) and air flowrate (2–8 LPM). Foam was controlled by the intermittent addition of a 50% solution of Antifoam B. Growth in the 10 L fermenter continued for 48±10 hours.

A 1000 L fermenter with a 800 L working volume was prepared by sterilizing 800 L of the Medium 1 at 121° C. for 45 minutes. 16 L of sterile filtered 500 g/L glucose was added aseptically to the 1000 L fermenter after autoclaving. Culture from the 10 L fermenter was aseptically transferred to the 1000 L fermenter. The fermenter was controlled at 30° C., pH 6.0 by addition of 2.5–5.0 N $H_2SO_4$ and 2.5–5.0 N NaOH, dissolved oxygen ≧50% air saturation by agitation rate (100–200 RPM), air flow rate (2–250 LPM), and/or back pressure control (0.2–0.4 bar). Foam was controlled by the intermittent addition of a 50% solution of Antifoam B. Production of 13-desmethoxy-FK520 ceased on day 5 and the fermenter was harvested. The fermentation broth was centrifuged at 20,500 g in an Alpha Laval AS-26 centrifuge.

EXAMPLE 3

Production of 13-Desmethoxy-13-methyl-FK-520

A 1 mL vial of KOS-60-135 working cell bank was thawed and the contents of the vial are added to 50 mL Medium 1 in a 250 mL baffled flask. The flask was placed in an incubator/shaker maintained at 30±1° C. and 175±25 RPM for 48±10 hours. The 50 mL culture was then added to a 2.8 L baffled flask containing 5(10 mL of Medium 1. This flask was incubated in an incubator/shaker at 30±1° C. and 175±25 RPM for 48±10 hours. The 500 mL culture was divided equally among ten 2.8 L baffled flasks each containing 500 mL of Medium 1. All flasks were then incubated as described previously. Medium 1 is the tryptic soy broth described in Example 2.

A 150 L fermenter was prepared by sterilizing 100 L of Medium 2 at 121° C. for 45 minutes.

| Medium 2 | |
|---|---|
| Component | Concentration |
| Corn starch | 16 g/L |
| Corn dextrin (type III) | 10 g/L |
| Soy flour | 15 g/L |
| Calcium carbonate | 4 g/L |
| Corn steep liquor (50%) | 5 g/L |
| Soy oil | 6 g/L |
| Sodium chloride | 2.5 g/L |
| Ammonium sulfate | 1 g/L |

After incubation, all 10 flasks were combined in a 5 L sterile inoculation bottle and aseptically added to a 150 L fermenter. The fermenter was controlled at 30° C., pH 6.0 by addition of 2.5 N $H_2SO_4$ and 2.5 N NaOH, dissolved oxygen ≧50% air saturation by agitation rate (50–600 RPM), air flow rate (10–50 LPM), and/or back pressure control (0.1–0.3 bar). Foam was controlled by the intermittent addition of a 50% solution of Antifoam B.

A 1000 L fermenter with a 700 L working volume was prepared by sterilizing 700 L of Medium 3 at 121° C. for 45 minutes.

Medium 3

| Component | Concentration |
| --- | --- |
| Corn starch | 35 g/L |
| Corn dextrin (type III) | 32 g/L |
| Soy flour | 33 g/L |
| Calcium carbonate | 8 g/L |
| Corn steep liquor (50%) | 12 g/L |
| Soy oil | 6 g/L |
| Sodium chloride | 7 g/L |
| Ammonium sulfate | 2 g/L |

Culture from the 100 L fermenter was aseptically transferred to the 1000 L fermenter. The fermenter is controlled at 30° C., pH 6.0 by addition of 2.5–5.0 N $H_2SO_4$ and 2.5–5.0 N NaOH, dissolved oxygen ≧50% air saturation by agitation rate (150–300 RPM), air flow rate (100–600 LPM), and/or back pressure control (0.1–0.4 bar). Foam was controlled by the intermittent addition of a 50% solution of Antifoam B. Production of 13-desmethoxy-13-methyl-FK520 ceases on day 5 and the fermenter was harvest,d. The fermentation broth was centrifuged at 20,500 g in an Alpha Laval AS-26 centrifuge.

EXAMPLE 4

Purification of 13-Desmethoxy-FK-520

Two sources of 13-desmethoxy-FK-520 was used for the purification procedure. The first source was centrifuged fermentation broth (1800 L) that was passed through a Sharples centrifuge (15,000 rpm) at a rate of 2 liters per minute. In addition, the whole broth was filtered through a Cuno filtration unit (model #16ZPC40F3T10CT) with 4 filter cartridges (10 µm pore size). The second source was 100% methanol extracted cell paste. The cell paste was obtained in 6 batches from the Sharples centrifuge bowl during centrifugation. The methanol extract was filtered through a Cuno filtration unit (model #16ZPC40F3T10CT) containing 4 filter cartridges (10 µm pore size). The centrifuged and filtered whole broth was loaded directly onto an HP20 column. The filtered methanol extract was prepared for load onto the HP20 column by adding deionized water to get a final concentration of 50% methanol. The two sources combined contained 7.4 g of 13-desmethoxy-FK-520. The 50% methanol solution was loaded on to the HP20 column after the whole broth. The HP20 sorbent was packed in an Amicon P350 Moduline chromatography column (35cm×20 cm). The HP20 column was loaded at 4 L/min and had backpressure under 5 psi.

Following loading, the column was washed with 50% methanol and product (13-desmethoxy-FK-520) was eluted with 5 column volumes (100 L) of 100% methanol. The product pool was evaporated using a Buchi rotary evaporator (R-152).

The solids from evaporation weighed 2 kilogram. The solids were dissolved in a minimal amount of 100% acetone, filtered and the filtrate was evaporated to dryness. This resulted in 357 grams of solids containing 3.4% 13-desmethoxy-FK520 by weight. The evaporated solids were further extracted with 60% methanol, filtered and the filtrate extracted again with 60% methanol. The 60% methanol extraction yielded 147 grams of solids of which 4.3% was 13-desmethoxy-FK-520 by weight.

The solids from methanol extraction were dissolved in 20 L of 50% addition of methanol then water and loaded onto an HP20SS column (8.9 cm×30 cm). The column was washed with 2 column volumes of 55% methanol. 13-desmethoxy-FK-520 was eluted with 3 column volumes of 60% methanol then 3 column volumes of 65% methanol. The best pool of fractions had a final volume of 9.2 L and contained 24 grams of solids. Product purity for this intermediate was 23%. Each fraction contains 0.5 column volumes each, and fractions were pooled to maximize the recovery of 13-desmethoxy-FK-520 based on HPLC chromatograms.

The best pool from HP20SS chromatography was diluted with 1.8 L of deionized water and loaded onto a 1 L C18 column (8.9 cm×16.5 cm). The C18 column was washed with 3 column volumes of 50% methanol and 6 column volumes of 60% methanol. The 13-desmethoxy-FK-520 was eluted with 10 column volumes of 70% methanol and 6 column volumes of 80% methanol. After C18 chromatography, fractions 20–36 was determined to be the best pool and contained 10.8 grams of solids, of which 50% was 13-desmethoxy-FK-520. Fraction 19 was the start of the 70% methanol elution.

The best pool 13-desmethoxy-FK-520 from the 1 L C18 chromatography was evaporated to dryness using the Buchi rotary evaporator (R-152) and extracted with dichloromethane. The extract was filtered and filtrate evaporated using a Buchi evaporater giving 9.9 grams of solids of which 48% was 13-desmethoxy-FK-520.

The solids from dichloromethane extraction was dissolved in 2.5 L of 50% methanol and loaded onto a 4.8 cm×20 cm C18 bakerbond column at 10 ml/min. The column was washed with one column volume of 50% methanol. The 13-desmethoxy-FK-520 was eluted with 6 column volumes of 85% methanol. Fractions 3–5 was determined be the best pool, where fraction 1 was the start of the 85% methanol elution. The best pool from this chromatography contained 4.43 grams of 13-desmethoxy-FK-520. The best pool was again diluted to a final volume of 2 L of 50% methanol and loaded onto the same column. The column was again washed with one column volume of 50% methanol. The 13-desmethoxy-FK-520 was eluted with 6 column volumes of 80% methanol. Fractions 4–11 were combined to make a 2 L pool. Overall yield was >65%. Other compounds of the invention that are produced from the fermentation of engineered host cells may be purified in a similar manner.

EXAMPLE 5

Characterization of 13-Desmethoxy-FK520

A 100-mg sample of partially purified 13-desmethoxy-FK520 (Example 4) was dissolved in 1000 uL of acetonitrile and insolubles were removed by centrifugation. The supernatant was purified by preparative HPLC using the following conditions: column=22×50 mm InertSil ODS-3 (MetaChem); flow rate=8.0 mL/min; solvent A=$H_2O$+0.1% acetic acid, solvent B=$CH_3CN$+0.1% acetic acid; gradient program: time 0=50%B, time 2=gradient to 100% B over 15 minutes, time 20=gradient to 90% B over 1 minute. Injections of 50 uL were made, and the separation was monitored by UV absorption at 240 nm. Two major peaks eluted, one broad peak corresponding to 13-desmethoxy-FK520 (ca. 15 minutes), and a sharp peak at 17 minutes corresponding to the oxepane rearrangement product.

The two major fractions were evaporated to dryness under vacuum. The residues were evaporated twice from acetonitrile to remove traces of acetic acid, then lyophilized from frozen benzene and dried overnight over KOH pellets under vacuum to yield 45 mg of pure 13-desmethoxy-FK520 and 20 mg of pure oxepane. NMR analysis indicated that each compound exists as a mixture of trans:cis amide rotamers.

TABLE 6

$^{13}$C—NMR data (CDCl$_3$, 300 K, 100 MHz):

| Carbon | FK520 Trans | FK520 Cis | 13-des(OMe)-FK520 Trans | 13-des(OMe)-FK520 Cis | 13-des(OMe)-FK520-oxepane Trans | 13-des(OMe)-FK520-oxepane Cis |
|---|---|---|---|---|---|---|
| 1 | 168.71 | 169.00 | 169.31 | 169.43 | 169.84 | 169.32 |
| 2 | 52.70 | 56.55 | 52.15 | 56.31 | 51.60 | |
| 3 | 26.20 | 27.60 | 26.64 | 26.47 | 25.49 | |
| 4 | 20.81 | 21.10 | 21.34 | 20.79 | 20.91 | |
| 5 | 24.48 | 24.55 | 24.94 | 24.38 | 25.20 | |
| 6 | 43.87 | 39.24 | 44.68 | 39.24 | 43.65 | |
| 8 | 165.78 | 164.70 | 165.93 | 164.77 | 167.40 | 167.02 |
| 9 | 192.66 | 196.13 | 196.33 | 195.76 | 98.24 | 98.14 |
| 10 | 98.64 | 97.06 | 98.93 | 98.36 | 210.13 | 209.83 |
| 11 | 33.62 | 34.57 | 34.84 | 34.94 | 43.29 | |
| 11-Me | 15.99 | 16.20 | 15.82 | 16.37 | 16.81 | |
| 12 | 32.53 | 32.68 | | | 35.46 | |
| 13 | 73.62 | 73.68 | 27.18 | | 27.37 | |
| 13-OMe | 56.07 | 56.29 | Missing | Missing | Missing | Missing |
| 14 | 72.22 | 72.86 | 73.84 | 70.54 | 77.00 | |
| 15 | 75.22 | | 82.14 | 81.55 | 83.04 | |
| 15-OMe | 56.96 | 57.54 | 57.89 | 57.71 | 57.54 | |
| 16 | 35.43 | 32.94 | 34.38 | | 32.86 | |
| 17 | 26.00 | 26.32 | 27.40 | | 29.74 | |
| 17-Me | 19.50 | 20.46 | 21.79 | 21.34 | 21.78 | |
| 18 | 48.46 | 48.66 | 47.01 | 48.83 | 48.24 | |
| 19 | 138.74 | 139.62 | 139.26 | 138.36 | 138.83 | 139.45 |
| 19-Me | 15.83 | 15.68 | 17.63 | 16.11 | 16.81 | |
| 20 | 123.34 | 123.06 | 124.53 | 122.98 | 123.69 | 123.69 |
| 21 | 54.93 | 54.67 | 54.94 | 54.12 | 54.52 | |
| 21a | 24.48 | 24.17 | 23.63 | 24.57 | 23.46 | |
| 21b | 11.67 | 11.67 | 11.70 | 11.56 | 11.67 | |
| 22 | 213.44 | 213.51 | 211.97 | 213.28 | 212.70 | 211.32 |
| 23 | 43.54 | 43.19 | 44.94 | 44.21 | 44.30 | |
| 24 | 69.03 | 70.04 | 67.74 | 69.88 | 69.61 | |
| 25 | 40.34 | 39.76 | 39.39 | 39.87 | 39.10 | |
| 25-Me | 9.78 | 9.48 | 9.93 | 9.41 | 9.59 | |
| 26 | 77.21 | 77.87 | 81.00 | 77.24 | 77.76 | |
| 27 | 131.78 | 132.32 | 130.50 | 131.84 | 131.43 | |
| 27-Me | 14.23 | 14.09 | 12.91 | 14.21 | 13.60 | |
| 28 | 129.61 | 129.70 | 132.97 | 129.46 | 130.44 | |
| 29 | 34.90 | 34.90 | 34.94 | 34.94 | 34.90 | |
| 30 | 34.74 | 34.84 | 34.38 | 34.48 | 34.58 | |
| 31 | 84.16 | 84.16 | 84.10 | 84.10 | 84.19 | |
| 31-OMe | 56.59 | 56.59 | 56.49 | 56.59 | 56.45 | |
| 32 | 73.54 | 73.54 | 73.41 | 73.47 | 73.48 | |
| 33 | 31.20 | 31.20 | 31.18 | 31.18 | 31.16 | |
| 34 | 30.62 | 30.62 | 30.45 | 30.63 | 30.46 | |

EXAMPLE 6

Purification of 13-Desmethoxy-13-methyl-FK-520

The starting material containing 417 mg of 13-desmethoxy-13-methyl-FK-520 was obtained from two sources. The first source was centrifuged and filtered fermentation broth (900 L). The Sharples centrifuge spun the fermentation broth at 15,000 rpm. The centrifuged broth then went through a Cuno depth filter containing four 10 μm filter cartridges at a rate of 2 L/min. The second source was from the 100 L of methanol used for extracting the product from the cell paste. The cells were extracted by adding 100 L of methanol to the cell paste and then stirring the solution for 3–4 hours. The resulting solution was then filtered through the same depth filter already containing the cell solids. The same 100 L of methanol was then recirculated through the filter apparatus for 60 minutes. The methanol in the filter was then expelled via air into a container at 2 L/min. The resulting methanol from the filter was diluted to a 50% methanolic solution using water.

The centrifuged and filtered fermentation broth (900 L) was passed through 18.3 L of HP20 sorbent packed into an Amicon P350SS Moduline 2 chromatography column. At 4 L/min loading, back pressure was found to be less than 5 psi. Following loading, the resin was washed with 200 L of the 50% methanolic solution made from the cell paste extract at a flow rate of 4 L/min. The 13-desmethoxy-13-methyl-FK-520 was eluted using 60 L of 100% methanol at a flow rate of 1 L/min.

The product pool was evaporated using a Buchi rotary evaporator (R-153). The 175 g of solids were dissolved in 2 L of 100% methanol, filtered and the filtrate evaporated to dryness. After the methanol extraction, 145 g containing 417 mg of 13-desmethoxy-13-methyl-FK-520 remained. The solids were extracted twice using 1 L of a 9:1 solution of hexane:acetone in a 20 L round bottom flask in a 40° C. water bath for 30 min. The solution was then filtered and the filtrate was rotovapped down to dryness. The resulting solids were crushed and then extracted for 30 minutes in a 20% solution of acetone in hexane in a beaker with vigorous mixing using a Lightning Labmaster mixer with an A310 rotor at 1000 rpm. The resulting solution was filtered and the filtrate contained 61.5 g of solids containing 0.7% 13-desmethoxy-13-methyl-FK-520 by weight. The filtrate was dried down and then resuspended in 4.10 L of 60% methanol.

The material then went through a 4.8 cm×26 cm Kontes chromatography column containing washed and equilibrated C18 sorbent at a rate of 100 ml/mim. The 13-desmethoxy-13-methyl-FK520 was then eluted with 85% methanol at a flow rate of 100 ml/min over 5 CV. Half column volume fractions were taken and like fractions, were pooled. The pools were then diluted to 60% methanol and the entire procedure was repeated for a total of 4 times. At the end of the 4$^{th}$ C18 chromatography step, 850 mg of solids containing 49% 13-desmethoxy-13-methyl-FK-520 by weight remained. Overall recovery at this step was 100%. The best pool was rotovapped down and redissolved in 1.36 L of 60% methanol. The solution was then loaded onto a 2.5 cm×56 cm Kontes chromatography column containing 275 ml of washed and equilibrated C18 sorbent at a flow rate of 25 ml/min. The material was then eluted with 85% methanol at the same flow rate over 12 column volumes. Fractions containing 13-desmethoxy-13-methyl-FK-520 were pooled and the chromatography was repeated once more. The best pool at the end of this step contained 419 mg of 13-desmethoxy-13-methyl-FK-520 with >50% purity. The best pool (1.84 L) was diluted to 60% methanol and reloaded onto a 4.8 cm×25 cm Kontes chromatography column containing washed and equilibrated C18 sorbent at a rate of 100 ml/min. The run was monitored by V at 210 nm and a heart cut of the major peak was taken.

The dried solids were then extracted twice (50 ml each) with hexane, dichloromethane, and methanol in that order. Each resulting solution was then rotovapped to dryness. The hexane solids and dichloromethane solids were pooled and assayed. After the material dried in the vacuum oven overnight, 526 mg of solids were left containing 358 mg of 13-desmethoxy-13-methyl-FK-520. The 13-desmethoxy- 13-methyl-FK-520 was found to be 68% pure by weight. Quantitation throughout all the purification was done by UV @ 210 nm and based on a 116 mg/L 13-desmethoxy-13-methyl-FK-520. Overall recovery was 86%.

EXAMPLE 7

HPLC Purification of 13-Desmethoxy-13-methyl-FK520

A 25-mg sample of partially purified 13-desmethoxy-13methyl-FK520 (Example 6) was dissolved in 250 uL of acetonitrile and insolubles were removed by centrifigation. The supernatant was purified by preparative HPLC using the following conditions: column=10×250 mm InertSil ODS-3 (MetaChem), flow rate=5.0 mL/min, solvent=90:10 $CH_3CN/H_2O+0.1\%$ acetic acid. Injections of 10–40 uL were made, and the separation was monitored by UV absorption at 240 nm. The major peak for 13-desmethoxy-13-methyl-FK520 eluted at 8.7 min. The product-containing fractions were pooled and evaporated to dryness under vacuum. The residue was evaporated twice from acetonitrile to remove traces of acetic acid, then lyophilized from frozen benzene and dried overnight over KOH pellets under vacuum to yield 15 mg of pure 13-desmethoxy-13-methyl-FK520.

EXAMPLE 8

General Purification Protocol

The following is a general purification protocol to recover a compound of the present invention that is produced via fermentation of host cells. The methanolic extract from a 20-L fermentation is concentrated to a volume of 200 mL, then poured slowly into 1500 mL of vigorously stirred ether. The resulting suspension is stored at 4 ° C. overnight, then filtered. The filtrate is concentrated, and the residue is redissolved in 200 mL of ether, dried over $MgSO_4$, filtered, and evaporated to yield an orange-colored syrup. This is dissolved in a minimal volume of $CH_2Cl_2$ and loaded onto a 35-g column of $SiO_2$ (ISCO) equilibrated in 80:20 hexanes/acetone. The column is eluted with 80:20 hexanes/acetone at a flow rate of 20 mL/min, collecting fractions of approximately 15 mL volume. After 10 minutes, the eluent is changed to 70:30 hexanes/acetone over 5 minutes, and elution is continued an additional 30 minutes. The fractions are analyzed by thin-layer chromatography (70:30 hexanes/acetone; staining using cerium-molybdate stain), and those fractions containing material with $R_f$ values similar to FK-520 are further analyzed by LC/MS. The product-containing fractions are pooled and evaporated. This material is dissolved in 1 mL of acetonitrile, diluted with 1 mL of water, and subjected to preparative HPLC using a 5 micron MetaChem InertSil ODS column (20×50 mm) equilibrated in 50:50 water/acetonitrile at a flow rate of 8 mL/min. Injections of 5 mg are made, and a linear gradient from 50:50 water/acetonitrile to 100% acetonitrile over 15 minutes is started after 1 minute. Elution is monitored by UV absorbance at 290 nm. The analogs typically elute as two peaks: the first peak is the FK-520 analog (10,14-hemiacetal), while the second peak is the oxepane analog (9,14-hemiacetal). The fractions containing the analog are pooled and evaporated to dryness.

Table 7 shows $^{13}$C-NMR data for selected compounds of the invention. The NMR data for FK-520 is included for comparison. 13-H, 15-H is 13, 15-desmethoxy-FK520. 13-Me, 15-OMe is 13-desmethoxy-13-methyl-FK-520. 13-H, 15-OMe is 13-desmethoxy-FK-520. 13-H, 15-Me is 13-desmethoxy-15-desmethoxy-15-methyl-FK-520. 13-H, 15-Et is 13-desmethoxy-13-methyl-15-desmethoxy-15-ethyl-FK-520.

TABLE 7

| position | FK-520 13C (maj) | FK-520 13C (min) | 13-H, 15-H 13C (maj) | 13-Me, 15-OMe 13C (maj) | 13-Me, 15-OMe 13C (min) | 13-H, 15-Me 13C (maj) | 13-H, 15-Me 13C (min) | 13-H, 15-Me 13C (maj) | 13-H, 15-Et 13C (maj) | 13-H, 15-Et 13C (min) |
|---|---|---|---|---|---|---|---|---|---|---|
| 1 | 169.0 | 168.7 | 169.5 | 169.2 | 168.9 | 169.3 | 169.3 | — | 169.4 | 169.0 |
| 2 | 56.6 | 52.7 | 52.4 | 56.6 | 52.5 | 52.2 | 56.3 | 52.4 | 52.3 | 56.2 |
| 3 | 27.6 | 26.2 | 26.4 | 27.6 | 26.3 | 26.8 | 27.7 | 26.7 | 27.0 | 28.1 |
| 4 | 21.1 | 20.8 | 21.5 | 21.1 | 20.8 | 21.3 | 20.8 | 21.3 | 21.3 | 20.9 |
| 5 | 24.2 | 24.5 | 25.0 | 24.2 | 24.2 | 24.9 | 24.4 | 25.0 | 25.0 | 24.3 |
| 6 | 39.2 | 43.9 | 45.0 | 39.2 | 43.9 | 44.7 | 39.2 | 44.8 | 44.6 | 39.3 |
| 8 | 164.7 | 165.8 | 165.8 | 164.7 | 166.0 | 165.9 | 164.8 | — | 166.0 | 165.4 |
| 9 | 196.1 | 192.7 | 196.9 | 196.1 | 193.6 | 196.3 | 195.8 | — | 196.7 | — |
| 10 | 97.0 | 98.7 | 98.7 | 97.0 | 99.1 | 98.9 | 98.4 | — | 98.8 | 98.0 |
| 11 | 34.6 | 33.6 | 35.1 | 34.9 | 34.7 | 34.9 | — | 35.1 | 34.9 | 34.7 |
| 11-Me | 16.2 | 16.0 | 16.0 | 16.3 | 16.0 | 15.8 | 16.4 | 15.9 | 15.8 | 16.5 |
| 12 | 32.7 | 32.5 | 27.0 | 36.9 | — | 34.5 | — | 36.4 | 28.8 | 28.9 |
| 13 | 73.7 | 73.7 | 30.1 | 30.6 | 30.5 | 27.0 | — | 26.8 | 26.9 | 27.8 |
| 13-R | 56.3 | 56.0 | na | 17.2 | 17.1 | na | na | na | na | na |
| 14 | 72.9 | 72.3 | 71.1 | 75.5 | 75.0 | 73.8 | 70.5 | 75.5 | 73.5 | 71.6 |
| 15 | 75.2 | 76.6 | 33.0 | 76.7 | 77.7 | 82.1 | 81.6 | — | 42.2 | 41.8 |
| 15-R | 57.0 | 57.5 | na | 57.0 | 57.1 | 57.9 | 57.7 | 16.3 | 21.4 | 21.3 |
| 15-R' | na | na | na | na | na | na | na | na | 10.7 | 10.7 |
| 16 | 33.0 | 35.5 | 30.4 | 32.9 | 35.0 | 34.4 | | 34.9 | 32.7 | — |
| 17 | 26.3 | 26.0 | 32.3 | 26.5 | 26.2 | 27.4 | 27.6 | 29.0 | 28.0 | — |
| 17-Me | 20.4 | 19.5 | 21.9 | 20.3 | 19.3 | 21.8 | 21.3 | 22.3 | 22.1 | 21.4 |
| 18 | 48.7 | 48.5 | 47.3 | 48.8 | 48.2 | 47.0 | 48.8 | 46.1 | 47.1 | 49.1 |
| 19 | 138.8 | 139.6 | 139.3 | 138.5 | 139.6 | 139.3 | 138.4 | — | 139.5 | 140.0 |
| 19-Me | 15.8 | 15.7 | 17.5 | 15.9 | 16.1 | 17.6 | 16.1 | 17.9 | 17.6 | 16.1 |
| 20 | 123.1 | 123.3 | 124.5 | 123.3 | 123.1 | 124.5 | 123.0 | 124.9 | 124.2 | 122.7 |
| 21 | 54.7 | 55.0 | 54.4 | 54.4 | 54.9 | 54.9 | 54.1 | 55.3 | 55.0 | 55.5 |
| 22 | 213.4 | 213.4 | 210.9 | 213.4 | 213.4 | 212.0 | 213.3 | — | 212.4 | — |
| 23 | 43.2 | 43.6 | 46.7 | 43.5 | 43.9 | 44.9 | 44.2 | 45.1 | 44.8 | 43.0 |

TABLE 7-continued

| position | FK-520 13C (maj) | FK-520 13C (min) | 13-H, 15-H 13C (maj) | 13-Me, 15-OMe 13C (maj) | 13-Me, 15-OMe 13C (min) | 13-H, 15-Me 13C (maj) | 13-H, 15-Me 13C (min) | 13-H, 15-Me 13C (maj) | 13-H, 15-Et 13C (maj) | 13-H, 15-Et 13C (min) |
|---|---|---|---|---|---|---|---|---|---|---|
| 24 | 70.0 | 69.0 | 66.0 | 70.2 | 69.2 | 67.7 | 69.9 | 67.6 | 67.8 | 69.6 |
| 25 | 39.8 | 40.4 | 39.2 | 39.9 | 40.1 | 39.4 | 39.9 | 39.4 | 39.3 | 39.0 |
| 25-Me | 9.6 | 9.9 | 10.0 | 9.6 | 9.9 | 9.9 | 9.4 | 10.0 | 10.0 | 8.3 |
| 26 | 77.2 | 77.9 | 83.2 | 77.2 | 77.9 | 81.0 | 77.2 | 82.1 | 81.8 | 78.1 |
| 27 | 132.3 | 131.8 | 130.5 | 132.4 | 131.8 | 130.5 | 131.8 | — | 130.3 | 131.9 |
| 27-Me | 14.1 | 14.2 | 12.3 | 14.1 | 14.2 | 12.9 | 14.2 | 12.8 | 12.7 | 14.3 |
| 28 | 129.7 | 129.6 | 134.8 | 129.8 | 129.6 | 133.0 | 129.5 | 133.9 | 133.4 | 129.2 |
| 29 | 34.9 | 34.9 | 35.0 | 34.9 | — | 34.9 | — | 35.1 | 35.0 | 35.0 |
| 30 | 34.9 | 34.8 | 34.4 | 34.9 | — | 34.5 | — | 34.6 | 34.4 | 34.4 |
| 31 | 84.2 | 84.2 | 84.2 | 84.2 | 84.2 | 84.1 | — | 84.3 | 84.1 | 84.1 |
| 31-methoxy | 56.6 | 56.6 | 56.5 | 56.6 | 56.6 | 56.5 | 56.6 | 56.8 | 56.5 | 56.6 |
| 32 | 73.5 | 73.5 | 73.5 | 73.6 | 73.6 | 73.4 | 73.5 | 73.8 | 73.5 | 73.5 |
| 33 | 31.2 | 31.2 | 31.2 | 31.3 | 31.3 | 31.2 | — | 31.4 | 31.2 | 31.2 |
| 34 | 30.6 | 30.6 | 30.4 | 30.6 | 30.6 | 30.4 | 30.6 | 30.8 | 30.4 | 30.6 |
| 35 | 24.5 | 24.5 | 23.3 | 24.6 | 24.6 | 23.6 | 24.6 | 24.2 | 23.2 | 24.6 |
| 36 | 11.6 | 11.7 | 11.7 | 11.7 | 11.7 | 11.7 | 11.6 | 11.9 | 11.7 | 11.7 |

EXAMPLE 9

Synthesis of 13-Desmethoxy-13-methyl-18-hydroxyl-FK-520

To a mixture of 13-desmethoxy-13-methyl-FK-520 (50 mg, 0.064 mmol) in 316 μL of $CH_2Cl_2$ was added a solution of $SeO_2$ (11 mg, 0.10 mmol) and t-BuOOH (84 μL, 0.46 mmol) in 63 μL of $CH_2Cl_2$ and 6 μL of $H_2O$ which were premixed until a clear solution was obtained. The reaction solution was stirred at ambient temperature for 2 days. The solvent was removed and the remaining residue was purified by column chromatography (30: 70 Ace-Hex) to yield 25 mg of the product as a white solid and 20 mg of the starting material.

EXAMPLE 10

Synthesis of 18-Ene-20-oxa-13-desmethoxy-13-methyl-FK-520

24,32-bis(t-Butyldimethylsilyl)-13-desmethoxy-13-methyl-FK-520:

13-Desmethoxy-13-methyl-FK-520 (110 mg, 0.142 mmol) was suspended in 1.77 mL of $CH_2Cl_2$ under a $N_2$ atmosphere. 2,6-Lutidine (83 mL, 0.709 mmol) and TBSOTf (131 mL, 0.568 mmol) were added and the resulting solution was stirred for 15 minutes. At this point, thin layer chromatography ("TLC") showed a complete consumption of the starting material. The reaction mixture was worked up by adding $NaHCO_3$ (50 mL) and extracting the product with $CH_2Cl_2$ (3×, 40 mL). The product was purified by column chromatography (75:25 hexanes/ethyl acetate) to give 125 mg (87%) of the desired product as a white foam. 1H NMR showed the presence of the TBS groups.

24,32-bis(t-Butyldimethylsilyl)-18-hydroxy-13-desmethoxy-13-methyl-FK-520:

A mixture of 24,32-bis(t-butyldimethylsilyl)-13-desmethoxy-13-methyl-FK-520 (125 mg, 0.124 mmol) in 191 mL of $CH_2Cl_2$ and 41 mL of EtOH was stirred with $SeO_2$ (14 mg, 0.124 mmol) and t-BuOOH (181 mL, 0.992 mmol) at room temperature. After 1.5 days, another portion of $SeO_2$ (14 mg, 0.124 mmol) and t-BuOOH (100 mL, 0.550 mmol) were added to the reaction mixture. The solution was stirred for 2 more days and worked up. The solvent was removed and the crude reaction mixture was purified by column chromatography (90: 10 hexanes/ethyl acetate-75:25 hexanes/ethyl acetate) to give 44 mg (35%) of the product as a white foam. Mass spectroscopy shows: 1003, 871, 853.

18-Ene-20-oxa-13-desmethoxy-13-methyl-FK-520:

A mixture of 24,32-bis(t-butyldimethylsylyl)-18-hydroxy-13-desmethoxy-13-methyl-FK-520 (37 mg, 0.036 mmol) in 1.5 mL of acetonitrile was treated with 0.5 mL of 2% aqueous HF/acetonitrile for 2.5 hours or until no starting material was detected by TLC. The reaction mixture was worked up by addition of ethyl acetate and aqueous saturated $NaHCO_3$. The product was extracted with ethyl acetate (4×40 mL) and purified by column chromatography (1:1 ethyl acetate/hexanes-60:40 ethyl acetate/hexanes) to give the title compound. The structure was determined by NMR spectroscopy.

EXAMPLE 11

Tris[1-(2-t-Butyldimethylsilyloxyethyl)indol-5-yl] bismuthane 1-(2-Hydroxyethyl)-5-bromoindole:

Under a $N_2$ atmosphere, 2-bromoethanol (17.6 g, 141 mmol) and 2-methoxypropene (10.0 g, 141 mmol) were stirred in 71 mL of THF at 0° C. for 30 minutes The resulting solution was added to a stirring mixture of 5-bromoindole (22.83 g, 116 mmol) and 60% NaH (4.62 g, 193 mmol) in 40 mL of DMF and 60 mL of THF. The solution was stirred at ambient temperature for 4 hours. The reaction mixture was worked up by quenching the excess of NaH with water and removing the aqueous layer. The organic layer was vigorously stirred with 200 mL of 2% aqueous phosphoric acid for 5 hours when the layers were separated. The organic layer was washed with water (2×200 mL) and the solvent removed. The residue was purified by column chromatography (30:70 EtOAc-Hex) to give 17 g of 1-(2-hydroxylethyl)-5-bromoindole.

Tris[1-(2-t-Butyldimethylsilyloxyethyl)indol-5-yl] bismuthane:

1-(2-hydroxyethyl)-5-bromoindole (2.08 g, 8.68 mmol), t-butyldimethylsilylchloride (1.44 g, 9.55 mmol), dimethylaminopyridine (11 mg, 0.087 mmol) and triethylamine (1.34 mL, 9.63 mmol) were dissolved in 20.7 mL of THF under $N_2$. The resulting solution was stirred at ambient temperature for 3 days. The mixture was cooled down and filtered under $N_2$. To this solution was added n-BuLi (5.46 mL, 8.73 mmol) and the solution stirred at −78° C. for 0.5 hours. A solution of $BiCl_3$ (958 mg, 3.04 mmol) in THF (5.0 mL) was added to the reaction mixture and the solution was stirred at −78° C. for another hour. The reaction mixture was worked up by addition of 1 g of cellulose suspended in 5 mL of THF and 0.65 mL of water. The supernatant was decanted and dried. The product was purified by column chromatography (5:95 EtOAc-Hex) to give the product as a white solid. Mp: 119–121° C.

EXAMPLE 12

Synthesis of 32-[1-(2-Hydroxyethyl)-indol-5-yl]-13-desmethoxy-13-methyl-FK-520

32-[1-(2-t-Butyldimethylsilyloxyethyl)-indol-5-yl]-13-desmethoxy-13-methyl-FK-520:

A solution of tris[1-(2-t-Butyldimethylsilyloxyethyl) indol-5-yl]bismuthane (80 mg, 0.077 mmol); benzoyl peroxide (17 mg, 0.071 mmol) and 2-butanone (0.965 mL) were stirred at ambient temperature for 1 day. To the solution was added 13-desmethoxy-13-methyl-FK-520 (38 mg., 0.049 mmol) and $Cu(OAc)_2$ (1 mg, 0.008 mmol) and the mixture was stirred for a day. The residue was dried and purified by column chromatography (10:90 EtOAc-Hex) to give 43 mg of product as a white foam.

32-[1-(2-Hydroxyethyl)-indol-5-yl]-13-desmethoxy-13-methyl-FK-520 (Also Referred to as 13-Desmethoxy-13-methyl-32-hydroxyethylindolyl-FK-520):

A solution of 32-[1-(2-t-butyldimethylsilyloxyethyl)-indol-5-yl]-13-desmethoxy-13-methyl-FK-520 (42 mg, 0.040 mmol) in 1.0 mL of MeOH and 40 μL of 1 N HCl was stirred at room temperature for about 3 hours. The reaction was worked up by removal of the solvent followed by column chromatography (25:75 EtOAc-Hex) to give 23 mg of product as a white solid.

EXAMPLE 13

Synthesis of 32-[1-(2-Hydroxyethyl)-indol-5-yl]-13-desmethoxy-FK-520

32-[1-(2-t-Butyldimethylsilyloxyethyl)-indol-5-yl]-13-desmethoxy-FK-520:

A solution of tris[1-(2-t-Butyldimethylsilyloxyethyl) indol-5-yl]bismuthane (81 mg, 0.079 mmol), benzoyl peroxide (18 mg, 0.07 mmol) and 2-butanone (0.875 mL) were stirred at ambient temperature for 1 day. To the solution was added 13-desmethoxy-FK-520 (40 mg., 0.051 mmol) and $Cu(OAc)_2$ (1.6 mg, 0.0088 mmol) and the mixture was stirred for a day. The residue was dried and purified by column chromatography (10:90 EtOAc-Hex) to give 23 mg of product as a white foam.

32-[1-(2-Hydroxyethyl)-indol-5-yl]-13-desmethoxy-FK-520:

A solution of 32-[1-(2-t-butyldimethylsilyloxyethyl)-indol-5-yl]-13-desmethoxy-FK-520 (23 mg, 0.022 mmol) in 0.89 mL mL of MeOH and 22 μL of 1 N HCl was stirred at room temperature for about 3 hours. The reaction mixture was diluted with $NaHCO_3$ and extracted with $CH_2CL_2$ (3×, 50 mL). The organic layer was removed and the residue was purified by column chromatagraphy (25:75 EtOAc-Hex) to give the product as a white solid.

EXAMPLE 14

FKBP-12 Binding Assay

Calcineurin (">95% pure by SDS/PAGE") was obtained from Calbiochem. Neutravidin® coated strip plates, pre-blocked with SuperBlock® were obtained from Pierce. [$^3$H]FK506 (87 Ci/mmol), labelled by saturation of the allyl group, was obtained from New England Nuclear. Synthetic RII peptide ($^+H_3$N-D-L-D-V-P-I-P-G-R-F-D-R-R-V-S-V-A-A-E-$CO_2$) was obtained from Peptides International Louisville, Ky.; www.pepnet.com). [γ-$^{32}$P]ATP (6000 Ci/mmol) was obtained from Pharmacia. ATP, cAMP, the catalytic subunit of protein kinase A, bovine brain calmodulin and human FKBP, expressed in *E. coli* were obtained from Sigma.

Wells of Neutravidin® coated strip plates were coated with 100μL of 1 μM biotinylated FKBP-12 (100 pmol) in 20 mM sodium phosphate, pH 7.4 for 2–4 hours at room temperature. Wells were rinsed with 3×200 μL PBS containing 0.2% Tween 20 (PBS-tween), then filled with 100 uL of PBS-tween containing 0.5 μM [$^3$H]FK-506 (4–5000 dpm/pmol, 150–200,000 dpm/assay) and 0–10 μM of competing ligand (unlabelled FK-506, FK-520, or 13-methyl-13-desmethoxy-FK-520). The mixture was incubated for 2 hours at 0° C., the solution was aspirated from the wells, and each well was quickly washed with 300 uL of ice cold PBS-tween. Wells were broken apart, placed in scintillation vials with 10 mL of Scintiverse BD and bound radioactivity was quantitated by scintillation counting. Data were fit to a competitive binding equation in which the $K_d$ of [$^3$H]FK-506 was assumed to be 0.4 nM:

$$dpmbound = maxdpmbound \left(1 - \left(\frac{[\text{competing ligand}]}{[\text{competing ligand}] + K_d(1 + [[^3H]FK506]/0.4 \text{ nM})}\right)\right)$$

to calculate the $K_d$.

EXAMPLE 15

Calcineurin Binding Assay

A peptide corresponding to residues 81–99 of the regulatory subunit of bovine type II cAMP-dependent protein kinase ("RII peptide") has been shown to be an optimal minimal substrate for calcineurin. The catalytic subunit of protein kinase A was used to transfer the labeled phosphate from [γ-$^{32}$P]ATP to serine-15 of the RII peptide. ATP was freshly dissolved in kinase buffer (40 mM MES, pH 6.5, 0.4 mM EGTA, 0.8 mM EDTA, 4 mM $MgCl_2$, 0.1 mM $CaCl_2$, 0.1 mg/mL BSA), quantitated spectrophotometrically ($\epsilon_{259}$= 15.4 $mM^{-1}$ $cm^{-1}$) and used to dilute the specific activity of [γ-$^{32}$P]ATP to ~5000 dpm/pmol. Phosphorylation reactions (200 uL) were performed in kinase buffer and contained 162 uM [γ-$^{32}$P]ATP, 150 uM RII peptide, 0.2 uM cAMP, 25 ug/mL (160 units) protein kinase A catalytic subunit. Reaction mixtures were incubated at 30° C. for 3.5 hours, then purified by solid phase extraction using a 3 mL (200 mg) Bakerbond C18 cartridge. The cartridge was equilibrated with 3 mL 30% acetonitrile/0.1% TFA followed by 5 mL of 0.1% TFA, the reaction mixture was loaded onto the column, washed with 20 mL of 0. 1% TFA, and the product was eluted with 4×1 mL of 30% acetonitrile/0.1% TFA. Fractions were collected and monitored by scintillation counting. Phosphopeptide containing fractions were pooled and evaporated to dryness by vacuum centrifugation. The phosphopeptide product were analyzed by HPLC using a 250× 4.6 mm Intertsil C18 column (Metachem) at 1 mL/min with a gradient from $H_2O$/pH 3 w/$H_3PO_4$ to 50% acetonitrile over 45 minutes. Separation between the RII peptide and phosphopeptide was monitored at 225 nm. Reversed phase HPLC using 0.1% TFA in a gradient of water to 50% acetonitrile over 45 minutes failed to resolve the starting peptide from the phosphopeptide product; however, the same column using a gradient from water/pH 3.0 w/H$_3$PO$_4$ to 50% acetonitrile over 45 minutes separated these compounds (RII peptide elutes at 17.4 min, phospho-RII peptide elutes at 19 minutes). Using this system, the phosphopeptide used in calcineurin assays was shown to contain <1% of nonphosphorylated peptide and have a radiochemical purity >95%.

To determine reaction parameters for initial rate assays, reaction mixtures (75 uL) containing 0–60 nM calcineurin and 80 nM calmodulin in calcineurin assay buffer (40 mM Tris, pH 7.5, 6 mM MgCl$_2$, 0.1 mM CaCl$_2$, 0.1 % BSA and 0.5 mM DTT) were initiated by addition of 1 uM phosphopeptide. The reactions were incubated at 30° C., and 10–25 uL aliquots were removed at 3, 12, 23, 47, 100, and 250 minutes and quenched with 0.5 mL 100 mM KPO$_4$/5% trichloroacetic acid ("TCA"). $^{32}$PO$_4$ was isolated from unreacted phosphopeptide using a dedicated 0.5 mL (bed volume) Dowex AG50X8 for each sample. The columns were prepared by resuspending the resin in water such that there was one volume of water above each volume of settled resin. The slurry (1 mL) was then pipetted into each column, followed by 10 mL of water. The bed volume was verified, then each column was washed with 1 mL 1 N NaOH, 2 mL 1 N HCl, and 4 mL water. Quenched reaction mixtures were applied to the columns, washed twice with 750 uL of water and the eluate was collected directly into scintillation vials. Scintiverse BD (15 mL) was added to each vial, and $^{32}$PO$_4$ was quantitated by scintillation counting.

The K$_i$ values for calcineurin phosphatase activity were determined in reaction mixtures containing 40 mM Tris, pH 7.5, 6 mM MgCl$_2$, 0.1 mM CaCl$_2$, 0.1% BSA and 0.5 mM DTT, 15 nM calcineurin and 30 nM calmodulin. For inhibition by FK-506 and FK-520, these molecules were included at ~6 uM and FKBP-12 concentration was varied from 0.01 uM to 2.5 uM. Following a 30 minute preincubation, reactions were initiated by addition of the phospho-RII peptide substrate to 1 uM and incubated at 30° C. Aliquots were removed at 3 and 35 minutes, quenched, and PO$_4$ release was measured as described above. Binding data were fit to an equation which corrects for depletion of the FKBP.compound complex by calcineurin binding:

$$Vi = Vo\left(1 - \left(\frac{([E]t + [S]t + Ki) - \sqrt{([E]t + [S]t + Ki)2 - 4[E]t[S]t}}{2[E]t}\right)\right)$$

Where V$_i$ is the observed rate, [S]$_t$ is the total concentration of FKBP.compound complex, [E]$_t$ is the total amount of calcineurin used, K$_i$ is the inhibition constant, and V$_o$ is the rate in the absence of inhibition.

The rate of phosphate hydrolysis in an illustrative set of calcineurin phosphatase assays was linear with calcineurin concentration in the range examined (0–60 nM). When 15 nM calcineurin was used, the reaction was linear for 45 min, using ~10% of the substrate.

EXAMPLE 16

Metabolism of 13-Desmethoxy-13-methyl-32-(2-hydroxyethylindolyl)-FK-520

A mixture containing FK species and a NADPH regenerating system was pre-incubated at 37° C. for 10 minutes before the reaction was commenced by the addition of the P-450 supersomes. The final concentrations of the components were: 100 mM potassium phosphate, pH 7.4; 3.3 mM MgCl$_2$; 3.3 mM glucose-6-phosphate; 1.3 mM NADP; 0.4 U/mL glucose-6-phosphate dehydrogenase; 200 pmole P-450/mL; and 20 µM FK species. Control reactions contained "mock" supersomes without 3A4 P-450 activity. Human 3A4 P-450 +Reductase supersomes (cat #P207) and vector control "mock" supersomes without 3A4P-450 (cat # P201) were obtained from Gentest Corporation (Woburn, Mass.).

Following addition of supersomes or mock supersomes, reactions were terminated at 0 minutes (immediately upon addition of P-450) and 30 minutes by addition of acetonitrile containing 0.1% acetic acid to 20% final acetonitrile concentration, followed by freezing immediately on dry ice. For reactions containing the 13-desmethoxy-13-methyl-32-(2-hydroxyethylindolyl)-FK analog, an equal volume of MeOH was added following addition of acetonitrile and the samples were immediately frozen on dry ice. The samples were clarified by centrifugation at 13,000 rpm for 5 minutes at 4° C. in a micro centrifuge prior to HPLC analysis.

The following HPLC program was employed: Column= MetaChem 0.46×15 cm intersil C18 column (5 µm); Solvent A=0.1% HOAc in water; Solvent B=0.1% HOAc in acetonitrile. Detection=UV (210 nm) and ELSD. Gradient: Equilibration with 20% B; injection (up to 1 ml), hold at 20% B for 5 minutes; linear gradient to 50% B in 5 minutes; linear gradient to 100 % B in 20 minutes; to 20% B in 1 minute; hold at 20% B for 10 minutes to equilibrate.

There was no change in peak area after 30 minutes when the FK analogs were incubated with mock supersomes. Hence, there was no time dependent loss of the parent compound due to (a) adsorption to proteins and membranes in the supersome preparation or (b) due to non-3A4 P-450 activities in the supersome preparation.

EXAMPLE 17

Biological Activities of Immunosuppressive Agents of the Present Invention

Table 8 summarizes the results of a FKBP binding assay, calcineurin inhibition assay and a P450 stability assay for FK-520 and a select number of the compounds of the present invention. Protocols for these assays are described in Examples 14–16.

TABLE 8

| Compound | FKBP Binding (Kd) | Calcineurin Inhibition Ki | P450% Stability (at 30 min) |
|---|---|---|---|
| FK-520 | 0.4 nM | 49 nM | 46 |
| 13-desmethoxy-FK-520 | 0.4 nM | 32 nM | 35 |
| 13-desmethoxy-13-methyl-FK-520 | 1.6 nM | 940 nM | 26 |
| 32-[1-(2-hydroxyethyl)-indol-5-yl]-13-desmethoxy-FK-520 | 16.3 nM | <15 nM | 72 |
| 32-[1-(2-hydroxyethyl)-indol-5-yl]-13-desmethoxy-FK-520 | 10.4 nM | 22 nM | 77 |

EXAMPLE 18

Biological Activities of Neurotrophic Agents of the Present Invention

Table 9 summarizes the results of nerve growth as using SH-SY5Y human neuroblastoma cells according to Gold et al., Exp Neuro, 147(2): 269–87 (1997) which is incorporated herein by reference. The assay measures the mean neurite length in μM that were induced at 0.1 nM and 10 nM of the compound of interested after 96 or 168 hours.

TABLE 9

| Compound | Neurite Length at 0.1 nM 96 h (μM) | Neurite Length at 0.1 nM 168 h (μM) | Neurite Length at 10 nM 96 h (μM) | Neurite Length at 10 nM 168 h (μM) |
|---|---|---|---|---|
| No treatment | 80 | 95 | — | — |
| Nerve Growth Factor | 143 | 169 | — | — |
| 18-hydroxy-13-desmethoxy-13-methyl-FK-520 | 168 | 191 | 132 | 165 |
| 18-ene-20-oxa-13-desmethoxy-13-methyl-FK-520 | 144 | 184 | 104 | 135 |

18-Hydroxy-13-desmethoxy-13-methyl-FK-520 is an ideal candidate for a neurotrophic agent because it does not also possess immunosuppressive activity. Although this compound binds FKBP with a $K_d$ of approximately 1.0 nM, it has a $K_i$ in the calcineurin inhibition assay of greater than about 14,000 nM.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A method to produce a compound comprising culturing a recombinant host cell selected from the group consisting of KOS45-170 (PTA-1811); KOS60-135 (PTA-1810); KOS132-188 (NRRL, 30460); KOS132-191 (NRRL 30461); KOS156-25 (NRRL 30462); KOS156-9A (NRRL, 30463); KOS16-9B (NRRL 30464); KOS156-26 (NRRL 30465); KOS156-33A (NRRL 30466); KOS156-33B (NRRL 30467); and KOS156-33C (NRRL 30468) under suitable conditions to produce the compound, wherein KOS45-170 (PTA-1811) produces

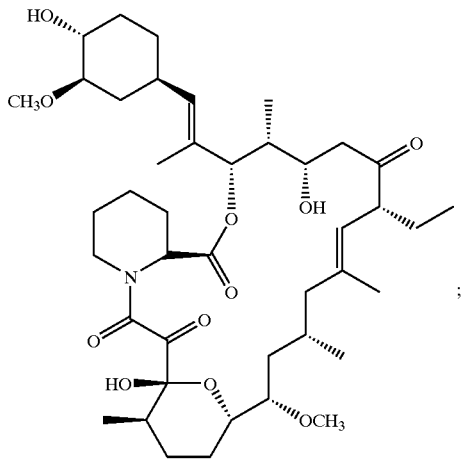

wherein KOS60-135 (PTA-1810) produces

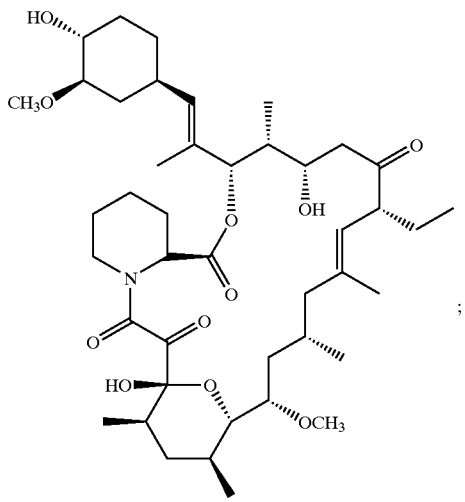

wherein KOS132-188 (NRRL 30460) produces

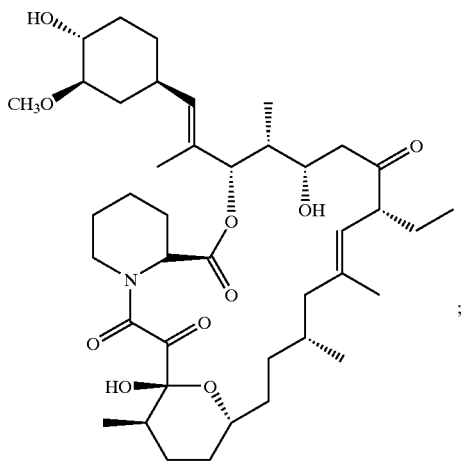

45
wherein KOS132-191 (NRRL 30461) produces
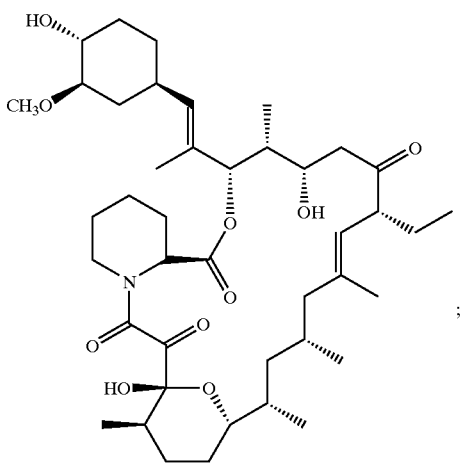
;
wherein KOS156-25 (NRRL 30462) produces
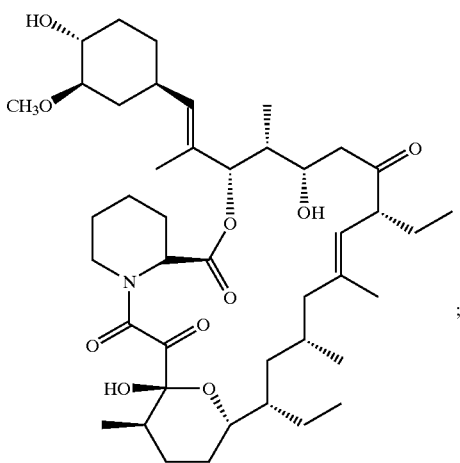
;
wherein KOS156-9A (NRRL 30463) produces
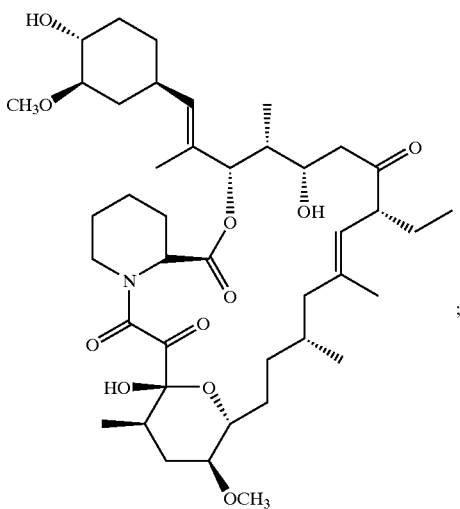
46
wherein KOS156-9B (NRRL 30464) produces
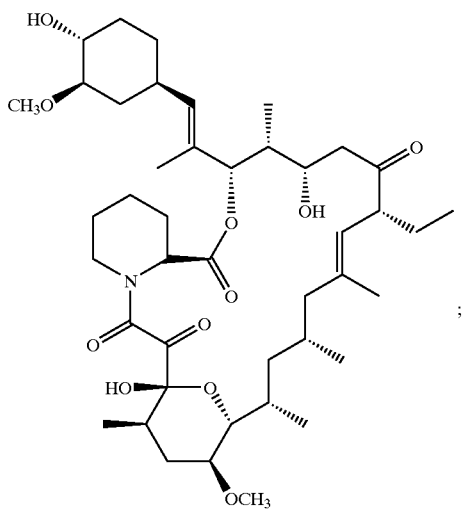
;
wherein KOS156-26 (NRRL 30465) produces
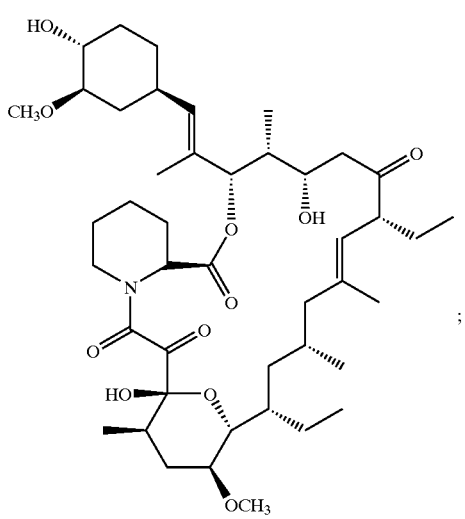
;
wherein KOS156-33A (NRRL 30466) produces
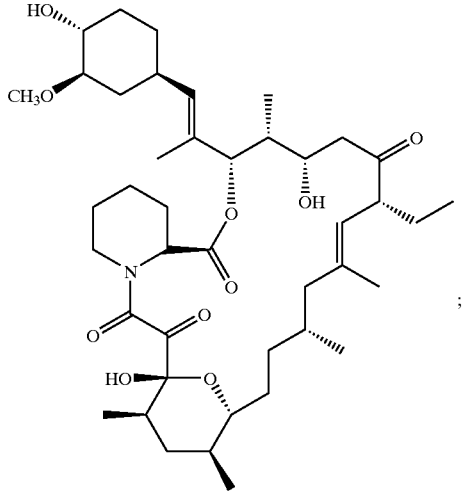
;

wherein KOS156-33B (NRRL 30467) produces

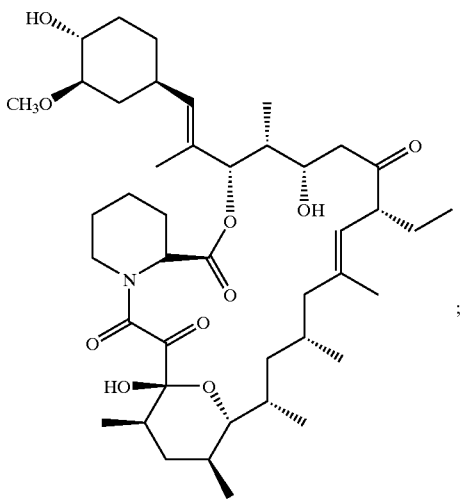

;

wherein KOS156-33C (NRRL 30468) produces

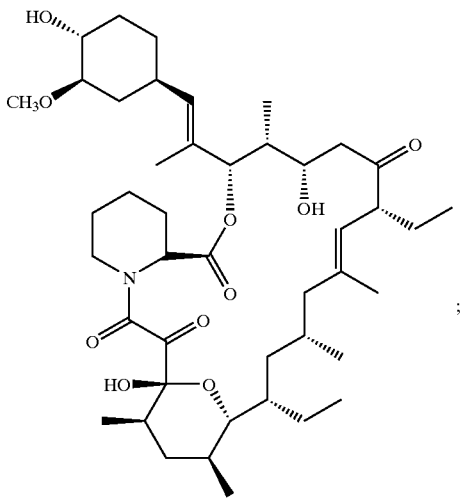

;

2. The method defined in claim 1 wherein the recombinant host cell is KOS45-170 (PTA-1811).

3. The method defined in claim 1 wherein the recombinant host cell is KOS60-135 (PTA-1810).

4. The method defined in claim 1 wherein the recombinant host cell is KOS 132-188 (NRRL 30460).

5. The method defined in claim 1 wherein the recombinant host cell is KOS 132-191 (NRRL 30461).

6. The method defined in claim 1 wherein the recombinant host cell is KOS 156-25 (NRRL 30462).

7. The method defined in claim 1 wherein the recombinant host cell is KOS156-9A (NRRL 30463).

8. The method defined in claim 1 wherein the recombinant host cell is KOS156-9B (NRRL 30464).

9. The method defined in claim 1 wherein the recombinant host cell is KOS156-26 (NRRL 30465).

10. The method defined in claim 1 wherein the recombinant host cell is KOS156-33A (NRRL 30466).

11. The method defined in claim 1 wherein the recombinant host cell is KOS156-33B (NRRL 30467).

12. The method defined in claim 1 wherein the recombinant host cell is KOS156-33C (NRRL 30468).

* * * * *